United States Patent [19]
Reed et al.

[11] Patent Number: 6,072,046
[45] Date of Patent: Jun. 6, 2000

[54] DIAZIRIDINYL-ARYL AND BIS-[DI(CHLOROETHYL)AMINO]-ARYL OLIGONUCLEOTIDE CONJUGATES AND REAGENTS FOR MAKING THE SAME

[75] Inventors: Michael W. Reed, Seattle; Igor V. Kutyavin; Eugeny A. Lukhtanov, both of Bothell; J. Ansel Wald, Seattle; Rich B. Meyer, Jr., Woodinville, all of Wash.

[73] Assignee: Epoch Pharmaceuticals, Inc., Redmond, Wash.

[21] Appl. No.: 09/136,779

[22] Filed: Aug. 26, 1998

[51] Int. Cl.⁷ .................... C07H 21/02; C07H 21/00; C07H 19/00; C12Q 1/68; A01N 43/04
[52] U.S. Cl. .................... 536/23.1; 435/6; 514/1; 514/44; 536/22.1; 536/25.3; 536/25.32; 536/26.6
[58] Field of Search .................... 435/6; 536/22.1, 536/23.1, 25.3, 25.32, 26.6; 514/1, 44

[56] References Cited

U.S. PATENT DOCUMENTS

| | | | |
|---|---|---|---|
| 5,177,196 | 1/1993 | Meyer, Jr. et al. | 536/22.1 |
| 5,419,966 | 5/1995 | Reed et al. | 428/406 |
| 5,446,137 | 8/1995 | Maag et al. | 536/23.1 |
| 5,512,667 | 4/1996 | Reed et al. | 536/24.31 |
| 5,591,575 | 1/1997 | Hampson et al. | 435/6 |
| 5,659,022 | 8/1997 | Kutyavin et al. | 536/22.1 |

FOREIGN PATENT DOCUMENTS

| | | | |
|---|---|---|---|
| 90/03370 | 4/1990 | WIPO | C07D 239/00 |
| 96/32496 | 10/1996 | WIPO | |
| 96/40711 | 12/1996 | WIPO | C07H 21/00 |

OTHER PUBLICATIONS

Millard et al. (1990) *J. Am. Chem. Soc.*, 112, 2459–2460.
Haworth et al., *Biochemistry*, 32, 12857–12863.
Nielsen et al., *Science*, 254 (1991) p. 1497.
Gottesfeld et al., *Nature*, 387 (1997) p. 202.
Robins et al., *Can. J. Chem.*, 60:554 (1982).
Robins et al., *J. Org. Chem.*, 48:1854 (1983).
Desmuck et al., *Bioconjugate Chemistry* (1995) 6, 578–586.
Griffey et al., *J. Med. Chem.* (1996) 39, 5100–5109.
Wiederholt et al., *J. Am. Chem. Soc.* (1996) 118, 7055–7062.
Wiederholt et al., *Bioconjugate Chemistry* (1997) 8, 119–126.
Gamper et al., (1993) *Nucleic Acid Research*, 21, 145–150.
Boger et al., *J. Org. Chem.* (1987), 52, 1521–1530.
Ausubel et al., *Current Protocols of Molecular Biology* vol. 1, Unit 3.10, "Phosphatases and Kinases", John Wiley & Sons, Inc. (1994–1998).

*Primary Examiner*—Jezia Riley
*Attorney, Agent, or Firm*—Klein & Szekeres, LLP

[57] ABSTRACT

Diaziridinyl-aryl and bis-[di(chloroethyl)amino]-aryl oligonucleotide conjugates have a sequence that is complementary in the triplex forming sense to a target sequence in duplex nucleic acid. The diaziridinyl-aryl and bis-[di(chloroethyl)amino]-aryl oligonucleotide conjugates effectively cross-link with both strands of the targeted duplex nucleic acid.

24 Claims, No Drawings

DIAZIRIDINYL-ARYL AND BIS-[DI(CHLOROETHYL)AMINO]-ARYL OLIGONUCLEOTIDE CONJUGATES AND REAGENTS FOR MAKING THE SAME

BACKGROUND OF THE INVENTION

1. Field of the Invention

The present invention is in the field of oligonucleotide and cross-linking group conjugates and in the field of reagents adapted for making such conjugates. More particularly, the present invention is in the field of diaziridinyl-aryl and bis-[di(chloroethyl)amino]-aryl oligonucleotide conjugates that can effectively cross-link with both strands of double stranded DNA, and in the field of reagents for making such conjugates.

2. Brief Description of the Prior Art

Agents capable of alkylating nucleic acids have been known in the prior art and have found application in chemotherapy, diagnostic and related fields and as genetic probes for molecular biology. Several drugs used in cancer chemotherapy are bifunctional alkylating agents, particularly bifunctional nitrogen mustards. Examples of clinically used nitrogen mustards are mechlorethamine, melphalan and chlorambucil. These have been shown to form interstand DNA cross-links with a preference for the DNA sequence 5'-GNC (Millard et al. (1990) J. Am. Chem. Soc. 112, 2459–2460). Diaziridinyl benzoquinones are another class of bifunctional alkylating agents that have been shown to form interstrand cross-links in DNA. The efficiency of interstrand cross-linking was increased by reducing the quinone to hydroquinone (Haworth et al. Biochemistry 32, 12857–12863).

The concept of covalently linking one or more alkylating functions to an oligonucleotide (ODN) to accomplish alkylation of a target sequence in nucleic acid which is complementary to the ODN, has also been known in the art. For example, published PCT application WO 96/40711 (published on Dec. 19, 1996) describes oligonucleotides covalently linked to alkylating functions which alkylate complementary nucleic acid, and under certain conditions cross-link two strands of double stranded nucleic acid. U.S. Pat. No. 5,659,022 describes covalently linked conjugates of ODNs with a cyclopropapyrroloindole moiety that alkylate nucleic acid sequences which are complementary to the base sequence of the ODN.

In view of the potential therapeutic, diagnostic, genetic probe and related applications there is still a need in the art for chemical reagents that can form interstrand cross-links with DNA more efficiently. Moreover, there is a need for covalently bonded ODN-cross linker conjugates which efficiently cross-link with complementary DNA, and especially for triple-strand-forming (TFO) ODN-cross linker conjugates which efficiently form interstrand covalent bonds with both strands of targeted ds DNA. The present invention provides such chemical reagents, ODN-cross-linker conjugates as well as reagents for preparing the ODN-cross-linker conjugates.

SUMMARY OF THE INVENTION

Covalently linked ODN-cross-linker conjugates are provided in accordance with the present invention which have the formula

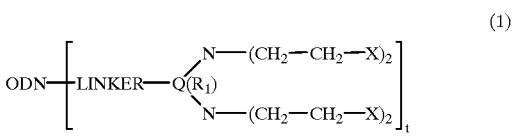

or the formula

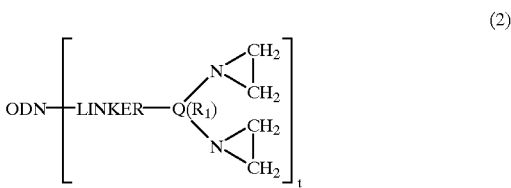

where X is a leaving group such as Cl, Br, or I;

Q is a 5 or 6 membered aromatic or quinone ring containing 0 to 3 heteroatoms independently selected from N, O and S, the Q ring being unsubstituted or substituted with one or more $R_1$ groups where $R_1$ is F, Cl, Br, I, alkyl, Oalkyl, Salkyl, Oalkenyl, Salkenyl, CO-alkyl, OH, O=, OCOalkyl, $N(R_3)_2$, NHCOalkyl, $SO_2$alkyl, COOH, COOalkyl, CN, $CF_3$, $NO_2$, tetrazol or aryl where $R_3$ is H or alkyl, the alkyl group includes 1 to 10 carbon atoms and includes branch-chained alkyl and cycloalkyl groups as well, and the alkenyl group includes 2 to 10 carbons and branch-chained alkenyl and cycloalkenyl groups as well.

t is an integer having the values between 1 and 3.

ODN is an oligonucleotide that may have a tail moiety attached at either of the 5' or 3' ends, or a side chain, and LINKER is a group having the length of 1 to 20 atoms, and which covalently connects the ODN to the Q ring, preferably through a tail moiety or through a side chain.

Chemical reagents suitable for being covalently bonded to an ODN or to a modified ODN having the aforesaid tail moiety or side chain are also provided in accordance with the present invention and have the formula

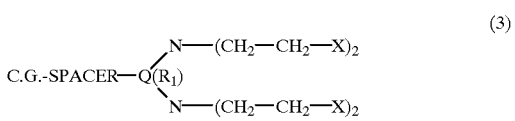

or the formula

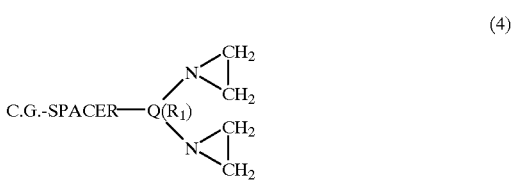

where the symbols are defined as above and C.G. stands for a conjugatable group, that is a group which is selectively reactive towards a functionality provided in the ODN, or in the derivatized ODN, to react with the ODN or with the derivatized ODN without significant loss of the di(chloroethyl)amino or aziridinyl cross-linking functionalities to provide the ODN-cross-linker conjugates of formula (1) or of formula (2). SPACER is that part of the LINKER defined above which is attached to the reagents (3) or (4).

The present invention also provides for diaziridinyl-aryl and bis-[di(chloroethyl)amino]-aryl DNA cross-linking agents which are covalently bonded to DNA targeting agents, such as intercalators or minor groove binders, in accordance with the formula

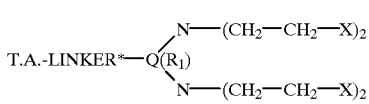

(5)

or the formula

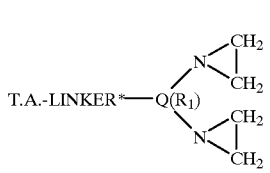

(6)

where T.A. stands for a DNA targeting group such as an intercalator or minor groove binder, the remaining symbols are defined as above except that the LINKER* group may be identical with the LINKER defined for formulas (1) through (4), or it may be substantially longer than a chain of approximately 20 atoms, in fact it may be a chain of up to approximately 60 atoms length when the T.A. group represents a minor groove binder. Other sequence specific DNA targeting agents include "peptide nucleic acids" Nielsen, et al. *Science,* 254 (1991) p 1497) and synthetic polyamides (Gottesfeld, et al. *Nature,* 387 (1997) p. 202). Simple polyamines such as spermine can also be used as T.A. The above-cited Nielsen et al. *Science* and Gottesfeld, et al. *Nature* references are expressly incorporated here by reference.

The ODN-cross-linker conjugates of the present invention selectively form triplexes with a target sequence in ds DNA that is complementary or substantially complementary to the ODN sequence in accordance with known triplex forming motifs, and efficiently cross-link with both strands of the ds DNA.

DETAILED DESCRIPTION OF THE INVENTION

General Embodiments

The prominent features of the novel oligonucleotide-cross-linker conjugates of the present invention are the nature of the oligonucleotide (ODN) itself and any tail, side chain and other moieties which may optionally be attached to it, the LINKER group and the diaziridinyl-aryl or bis-[di (chloroethyl)amino]-aryl cross-linking groups being attached to the ODN through the LINKER, as shown in formulas (1) and (2).

The ODN in accordance with the present invention has a base sequence that is complementary to a target sequence in a targeted nucleic acid. The ODN-cross-linker conjugate of the invention may be targeted to single stranded nucleic acid, in which case the ODN sequence is complementary to the target sequence in the conventional Watson Crick sense. The ODN-cross-linker conjugate of the invention may also be targeted to a sequence in double stranded (ds) nucleic acid and contemplated to react with the ds nucleic acid in the presence of a recombinase enzyme, in analogy to the reaction described in published PCT application WO 96/40711 which is incorporated herein by reference. In the latter case also, the sequence of the ODN is complementary to the target under the conventional Watson Crick base pairing rules. In the preferred embodiments of the ODN-cross-linker conjugates of the invention, however, the ODN is designed as a triplex forming oligonucleotide (TFO) to complex with homopurine runs in ds nucleic acid pursuant to the well known G/A, C/T and or the G/T motif, and thereafter cross-link with both strands of the ds DNA, primarily at a GNC site (N stands for any nucleotide).

The length of the ODN portion of the ODN-cross-linker conjugate of the invention is limited only in the sense that the ODN must be complementary in the senses described above to a target sequence. Generally speaking, the ODN may contain approximately 6 to 500 nucleotides, more preferably approximately 6 to 200 nucleotides even more preferably 6 to 100 nucleotides. For the preferred embodiment, however where complexing is with homopurine or substantially homopurine runs in ds nucleic acid, the length of the target sequence in ds DNA or duplex is limited only in the sense that for most practical applications and uses the ds DNA (or part or fragment thereof) is naturally occurring, or is derived from naturally occurring DNA, and that in natural DNA homopurine sequences (or sequences containing substantially only purines) rarely reach, let alone exceed 40 bases. A lower practical limit for the possible target sequence is approximately 6 purine bases, primarily because it is difficult to achieve effective triplex formation to a homopurine sequence that is shorter than approximately 6 bases. As it should be apparent from the foregoing, the triplex forming ODN-cross-linker conjugate of the present invention itself is single stranded.

In addition to the sequence in the ODN which is complementary, or substantially complementary to the homopurine (or substantially homopurine) run of the target in the ds DNA, the complementary sequence of the ODN may also contain at its 3' or 5' end, or at both ends, an "overhang" comprising one or several nucleotides. A practical limit on the length of the one or two overhangs is merely that the overhangs must not interfere significantly with the triplex formation and subsequent cross-linking reaction between the target sequence of the ds DNA and the complementary sequence of the ODN. Based on the foregoing considerations a most preferred length of the ODN-cross-linker conjugates of the preferred embodiments that target homopurine runs in ds nucleic acid is between approximately 6 to 100 nucleotides.

In the presently preferred embodiments of the ODNs of the invention the sugar or glycosidic moieties are 2-deoxyribofuranosides in the natural (β) configuration and all internucleotide linkages are the naturally occurring phosphodiester linkages. In alternative embodiments however, instead of 2-deoxy-β-D-ribofuranose β-D-ribofuranose may be present where the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose). Alternatively, the sugar-phosphate backbone of the ODNs of the present invention may comprise α-D-arabinofuranosides. ODNs containing α-D-arabinofuranosides can be obtained in accordance with the teachings of U.S. Pat. No. 5,177,196, the specification of which is expressly incorporated herein by reference The phosphate backbone of the ODNs of the invention may also be modified so that the ODNs contain phosphorothioate, phosphoramidate, and/or methylphosphonate linkages.

The ODNs of the present invention may also have intercalators, lipophilic groups, minor groove binders, reporter groups, and/or chelating agents attached either to one or more of the internally located nucleotide bases, or to the 3' or 5' phosphate end, or to both ends. The nature and attachment of intercalator, lipophilic groups, minor grove binders, reporter groups and chelating agents to oligonucleotides are presently well known in the state-of-the-art, and are described for example in U.S. Pat. Nos. 5,512,667, 5,419,966 and in the publication WO 96/32496, which are incorporated herein by reference.

The ODNs of the invention may also have a relatively low molecular weight "tail moiety" attached either at the 3' or 5' end, or at both ends. By way of example a tail moiety may be a phosphate, a phosphate ester, an alkyl group, an aminoalkyl group, or a lipophilic group. Generally speaking, the tail moiety may also link the intercalators, lipophilic groups, minor groove binders, reporter groups, chelating agents and the cross-linking functionalities shown in formulas (1) through (6) to the ODNs of the invention. Again, generally speaking the nature of tail moieties and methods for obtaining ODNs with various tail moieties are also described in the above-referenced U.S. Pat. Nos. 5,512,667 and 5,419,966.

In the preferred embodiments of the oligonucleotide-cross-linker conjugates of the present invention the LINKER and the cross-linking functionality itself are attached to the ODN through a tail moiety. In the preferred embodiments the nature of the tail moiety plays a specific role in the synthesis of the oligonucleotide-cross-linker conjugate itself, in that a nucleophilic amino group of the tail is utilized to react selectively with a "conjugatable group" of the reagents of formulas (3) and (4) to form the oligonucleotide-cross-linker conjugate without reacting with the diaziridinyl-aryl or bis-[di(chloroethyl)amino]-aryl alkylating groups. This is described in detail below.

With regard to the possible variations of the nucleotide units, the "phosphate backbone", "tail" and various appendages such as intercalators, lipophilic groups, minor groove binders, reporter groups and chelating agents of the ODNs of the present invention, the following should be kept in mind. The only limitation in this regard is that these groups must not interfere significantly with binding of the ODN-cross-linker conjugates to their respective intended target; specifically in the preferred embodiment they must not interfere significantly with the triplex formation between the ODN and the target sequence of the ds DNA.

Referring now to the group designated LINKER in formulas (1) and (2) the function of this group or moiety is to covalently attach the diaziridinyl-aryl or bis-[di(chloroethyl) amino]-aryl cross-linking groups to the ODN. The LINKER may be attached to either terminus of the ODN, may be attached to a heterocyclic base of the ODN, may be attached to the 4' or 2' position of the sugar moiety, or to an intermediate phosphate ester group in the ODN. The LINKER maintains the diaziridinyl-aryl or bis-[di (chloroethyl)amino]-aryl cross-linking functions at a desired distance and steric position relative to the ODN and poised for cross-linking with nucleophilic target sequence in the targeted nucleic acid. Thus, conceptually the LINKER is a single entity that is not itself reactive under conditions of hybridization and cross-linking when the LINKER is incorporated into the conjugates of formula (1) and (2). As noted above, the LINKER does not exceed the length of a chain of approximately 20 carbon atoms. In practice, as a result of the manner in which the ODN-conjugates of the invention are synthesized, the LINKER is usually comprised of two parts or moieties. Before completion of the ODN-conjugate molecule one of these parts or moieties is usually attached to the ODN, in preferred embodiments to the tail of the ODN, and the other part or moiety is the SPACER attached to the cross-linker diaziridinyl-aryl or bis-[di(chloroethyl)amino]-aryl cross-linking group combination as shown in (3) and (4). It will be readily understood by those skilled in the art on the basis of the foregoing that the entire LINKER, as depicted in formulas (1) and (2) is usually a result of a coupling reaction between the two moieties of the LINKER, and includes a function "Y" that is called a "functional linking group". Thus, exemplary and more specific formulas for the LINKER function are

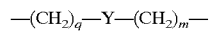

where m and q are defined such that the total length of the linker does not exceed approximately 20 atoms, the —(CH$_2$)$_q$— is the part of the LINKER which is attached to the ODN, and —(CH$_2$)$_m$— is the SPACER attached to the DNA-cross-linking agent.

Usually and preferably the Y functional linking group is an amide group (—NHCO—) that is the result of a reaction between a terminal amino group attached to the ODN and a reactive function, designated C.G. in formulas (3) and (4) attached to the cross-linking agents. In fact, in accordance with the present state of synthetic methodology, the ODN-diaziridinyl-aryl conjugates of the invention of formula (2) can only be practically synthesized with an amide function included in the LINKER. This will become more apparent as a result of the description of the specific examples or embodiments and their synthesis. The LINKER including the amide function is also preferred for the ODN-bis-[di (chloroethyl)amino]-aryl conjugates of formula (1) of the invention.

More broadly or generally speaking however, the LINKER or SPACER may contain alkylene groups of the formula —(CH$_2$)$_{n'}$— (where n' is 1 to approximately 20). The alkylene groups may be modified to include one or more double bonds to render it an alkenylene moiety having 2 to approximately 20 carbon atoms and one or more double bonds. Alkyne groups can also be used in the LINKER. The LINKER or SPACER may incorporate into the basic alkyl or alkenyl chain one or more ether, thioether, peptide (amide) or ester linkages, a keto function, one or more phosphate ester functions and/or an aromatic (primarily phenyl or substituted phenyl) rings, or combination of the foregoing.

Other examplary and even more specific formulas for the LINKER are

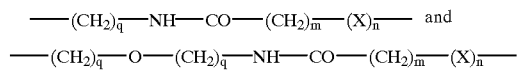

where the parameters m, n, p, and q are defined such that the total length of the LINKER does not exceed approximately 20 atoms, X is aryl (phenyl, furanyl, pyranyl, thienyl, preferably phenyl) or simple substituted aryl (such as fluoro, chloro, bromo, lower alkyl or lower alkoxy substituted aryl), and the X group may occupy a location other than the ones indicated in the preceding formulas.

Still further specific examples for the LINKER with different functional linker groups are:

—(CH$_2$)$_m$SCH$_2$CO(CH$_2$)$_n$—

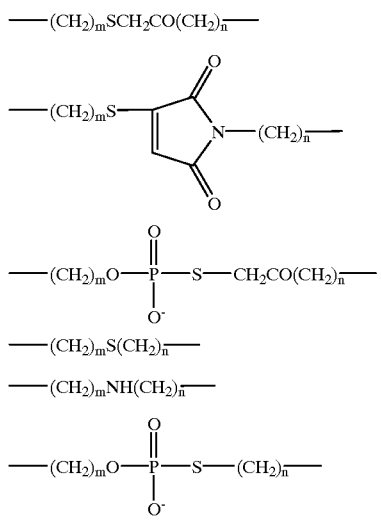

—(CH$_2$)$_m$O—P(=O)(O$^-$)—S—CH$_2$CO(CH$_2$)$_n$—

—(CH$_2$)$_m$S(CH$_2$)$_n$—

—(CH$_2$)$_m$NH(CH$_2$)$_n$—

—(CH$_2$)$_m$O—P(=O)(O$^-$)—S—(CH$_2$)$_n$— where the parameters m and n are defined again such that the overall length of the LINKER does not exceed that of a chain of approximately 20 atoms. Among all of the foregoing specific LINKER structures those are preferred which include an amide as the functional linker group. As explained above, the latter is formed when a moiety terminating in a nucleophilic amino group attached to the ODN reacts with the reagent shown in the formulas (3) and (4) where C.G. is an active ester. This type of attachment of the diaziridinyl-aryl or bis-[di(chloroethyl)amino]-aryl cross-linking groups through the SPACER group to a "tail" at either end of the ODN, and specifically to an aminoalkyl tail of the ODN is described below in detail in the description of the preferred embodiments or examples. Additionally, as noted above, in other embodiments the diaziridinyl-aryl or bis-[di(chloroethyl)amino]-aryl cross-linking groups can be attached to a heterocyclic base, for example to the uracil moiety of a 2'-deoxyuridylic acid building block of the ODN. Such a modified uracil moiety may take the place of a thymine (T) that would otherwise be present in the ODN. The linkage can occur through the intermediacy of an amino group, that is, the LINKER-diaziridinyl-aryl or LINKER-bis-[di(chloroethyl)amino]-aryl cross-linking group combination may contain to a 5-alkylamino-2'-deoxyuridylic acid unit of the ODN.

In still other embodiments the LINKER-diaziridinyl-aryl or LINKER-bis-[di(chloroethyl)amino]-aryl cross-linking group combination is attached to the 5-position of the 2'-deoxyuridylic acid building unit of the ODN by a carbon-to-carbon bond. Generally speaking, 5-substituted-2'-deoxyuridines can be obtained by an adaptation of the general procedure of Robins et al. (Can. J. Chem., 60:554 (1982); J. Org. Chem., 48:1854 (1983)). In accordance with this adaptation, palladium-mediated coupling of a substituted 1-alkyne to 5-iodo-2'-deoxyuridine gives an acetylene-coupled product. The acetylenic dUrd analog is reduced, with Raney nickel for example, to give the saturated compound, which is then used for direct conversion to a reagent for use on an automated DNA synthesizer. Examples of reagents which can be coupled to 5-iodo-2'-deoxyuridine in accordance with this method are HC≡CCH$_2$OCH$_2$CH$_2$N(CO)$_2$C$_6$H$_4$ (phthalimidoethoxypropyne) and HC≡CCH$_2$OCH$_2$CH$_2$NHCOCF$_3$ (trifluoroacetamidoethoxypropyne). In these examples the nucleosides which are obtained in this scheme are incorporated into the desired ODN, and the reagent in accordance with formula (3) or (4) is attached to the terminal amino group only after removal of the respective phthalic or trifluoroacetyl blocking groups.

Other examples of nucleotides where the LINKER-diaziridinyl-aryl or LINKER-bis-[di(chloroethyl)amino]-aryl cross-linking group combination is attached to a heterocyclic base, are 2'-deoxy-4-aminopyrazolo[3,4-d]pyrimidine derivatives. These compounds can be made in accordance with the teaching of published PCT application WO: 90/03370 (published on Apr. 5, 1990 and incorporated herein by reference). In these compounds the crosslinking arm is attached at the 3-position, which is equivalent to the 7-position of purine.

In still other embodiments, the LINKER-diaziridinyl-aryl or LINKER-bis-[di(chloroethyl)amino]-aryl cross-linking group combination is attached to the 4' position of a sugar moiety. This can be accomplished by appropriate adaptation of the teachings of U.S. Pat. No. 5,446,137 (Maag et al.). In still further alternative embodiments the LINKER-diaziridinyl-aryl or LINKER-bis-[di(chloroethyl)amino]-aryl cross-linking group combination is attached to the 2' position of the sugar moiety. This can be accomplished for example, by appropriate adaptation of the teachings of Desmuck et al. Bioconjugate Chemistry (1995) 6, 578–586 and Griffey et al. J. Med. Chem. (1996) 39, 5100–5109.

Attachment to an intermediate phosphate can be accomplished, for example by adapting the teachings of Wiederholt et al. J. Am. Chem. Soc. (1996) 118, 7055–7062 and Wiederholt et al. Bioconjugate Chemistry (1997) 8, 119–126.

Referring now to the diaziridinyl-aryl and bis-[di(chloroethyl)amino]-aryl cross-linking groups, shown in formulas (1) through (6), as applicable, the aromatic group designated Q is preferably a phenyl group or a 1,4-quinone (para quinone) or a 1,4-hydroquinone. Because of the nature of the nitrogen mustard alkylating groups of formulas (1), (3) and (5) and of the aziridinyl groups of formulas (2), (4) and (6) the reactivity towards a nucleophile, such as the N-7 position of guanine in a target nucleic acid, is significantly influenced by the electron donating or electron withdrawing nature of substituents on the aromatic ring Q, and by the nature of the aromatic ring itself. Thus, the speed and efficiency of alkylation/cross-linking by the compounds of the invention can be "tuned" by the judicious selection of the nature of the Q ring itself, and by the nature, number and position of the substituents $R_1$ in the aromatic ring. Because the LINKER (or SPACER) is also a "substituent" of the aromatic ring Q, the electron donating or electron withdrawing nature and position of the LINKER also influences the reactivity of the diaziridinyl-aryl and bis-[di(chloroethyl)amino]-aryl cross-linking groups. In this regard it will be readily understood by those skilled in the art that electron donating substituents tend to increase the reactivity of the diaziridinyl-aryl and bis-[di(chloroethyl)amino]-aryl cross-linking groups, and electron withdrawing groups tend to decrease their reactivity.

In the herein described specific embodiments, phenyl groups having no $R_1$ substituent (other than the LINKER) are preferred for the ODN-conjugates having the bis-[di(chloroethyl)amino]-aryl cross-linking groups. For the ODN-conjugates having the diaziridinyl-aryl cross-linking groups alkyl, more preferably methyl, substituted 1,4-quinones are preferred. The number of cross-linkers attached in the preferred embodiments is one, so that the preferred value of t=1.

The "conjugatable group" shown in formulas (3) and (4) and abbreviated there as "C.G." is a reactive group that is attached to the cross-linking group via the SPACER and reacts with an appropriate reactive group linked to the ODN to covalently bond the cross-linker groups to the ODN under condition which do not substantially affect the otherwise reactive diaziridinyl-aryl and bis-[di(chloroethyl)amino]-aryl cross-linking groups. Thus, selective reactivity between an appropriate reactive group on the ODN and the "conjugatable group" is important. It has been found that these conditions are best satisfied when the reactive group of the ODN is a nucleophilic amino group, and the "conjugatable group" is a good leaving group attached to an electrophilic center in the SPACER. Preferably, the conjugatable group is a group that forms an active ester with the adjoining carbonyl (CO) group of the SPACER. Preferred examples for the conjugatable group are 2,3,5,6-tetrafluorophenyloxy (TFP) and para-nitrophenyloxy (PNP).

In the preferred examples of the ODN-conjugates of the invention the LINKER contains an aminoalkyl tail of the ODN. As noted above, aminoalkyl, and specifically aminohexyl tailed ODNs can be readily synthesized in accordance with the prior art, for example as disclosed in U.S. Pat. Nos. 5,512,667 and 5,419,966. The active esters which include as the leaving group the 2,3,5,6-tetrafluorophenyloxy (TFP) or para-nitrophenyloxy (PNP) groups, combined with SPACER moieties of the preferred embodiments provide an exceptionally good combination for selective reactivity that allows formation of the ODN-conjugates within the scope of formulas (1) and (2), by reaction of a 5' aminohexyl tailed ODN with reagents wherein the "C.G.-SPACER- and cross-linking agent" combination thus represents the specific preferred examples as shown by formulas (7) through (10). In these $R_4$ is 2,3,5,6-tetrafluorophenyloxy or para-nitrophenyloxy. In formula (11) the cross-linking functionality is not within the scope of the invention because there is only one "nitrogen mustard" (di(chloroethyl)amino group) attached to the phenyl group. The reagent of formula (11) was prepared for purposes of comparison.

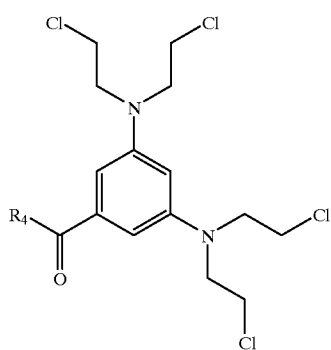

(7)

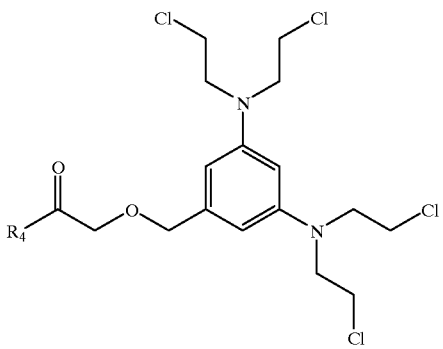

(8)

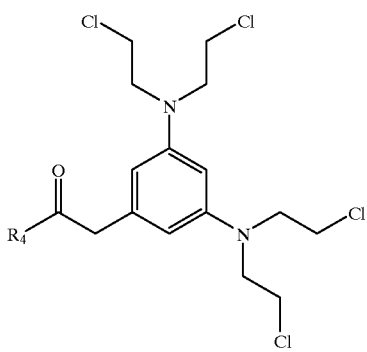

(9)

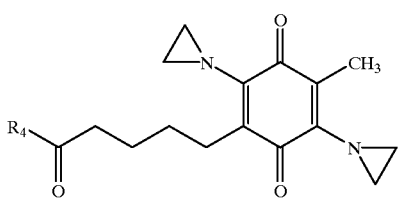

(10)

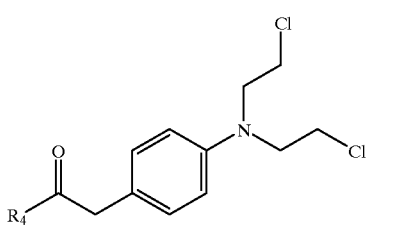

(11)

Referring now to the DNA targeting group designated T.A. in formulas (5) and (6), these are intercalator and minor groove binder groups of the type well known in the art. For specific description of intercalator groups repeated reference is made to the above-cited U.S. Pat. Nos. 5,512,667, 5,419, 966. Like intercalators, minor groove binders per se are well known and a general description can be found for example in the publication of WO 96/32496 and in U.S. application Ser. No. 08/415,370 filed on Apr. 3, 1995 which has been allowed and the issue fee has been paid. The specifications of WO 96/32496 and of U.S. application Ser. No. 08/415,370 are expressly incorporated herein by reference.

The group linking the minor groove binder moiety to the diaziridinyl-aryl and bis-[di(chloroethyl)amino]-aryl cross-linking groups can be within the scope of the above description of the LINKER groups of formulas (1) and (2), but may also be substantially longer, up to a length equivalent to a chain of approximately 60 atoms. The compounds of formulas (5) and (6) cross-link with nucleic acids efficiently and may be used in therapeutic, diagnostic, genetic probe and related applications.

Specific Embodiments and Demonstration of Cross-Linking Ability

Specific bis-[di(chloroethyl)amino]-phenyl compounds of the invention, having a suitable SPACER and 2,3,5,6 tetrafluorophenyl (TFP) or para nitrophenyl (PNP) ester reactive groups that render them suitable for coupling with an "amino-tailed" ODN are shown by formulas as Compounds 1 through 3. A specific diaziridinyl-1,4-benzoquinone compound of the invention also having a suitable SPACER and a 2,3,5,6 tetrafluorophenyl (TFP) or para nitrophenyl ester reactive group that renders it suitable for coupling with an "amino-tailed" ODN and with intercalators or with minor groove binders, is shown by formula as Compound 4. The specific diaziridinyl-1,4-benzoquinone moiety of the invention covalently attached to a 9-aminoacridine intercalator moiety is shown as Compound 5. In Compound 6 the same is attached to a well known minor groove binder moiety designated Me-CDPI$_2$. Synthesis of these compounds is described below in detail in the Experimental Section of this application.

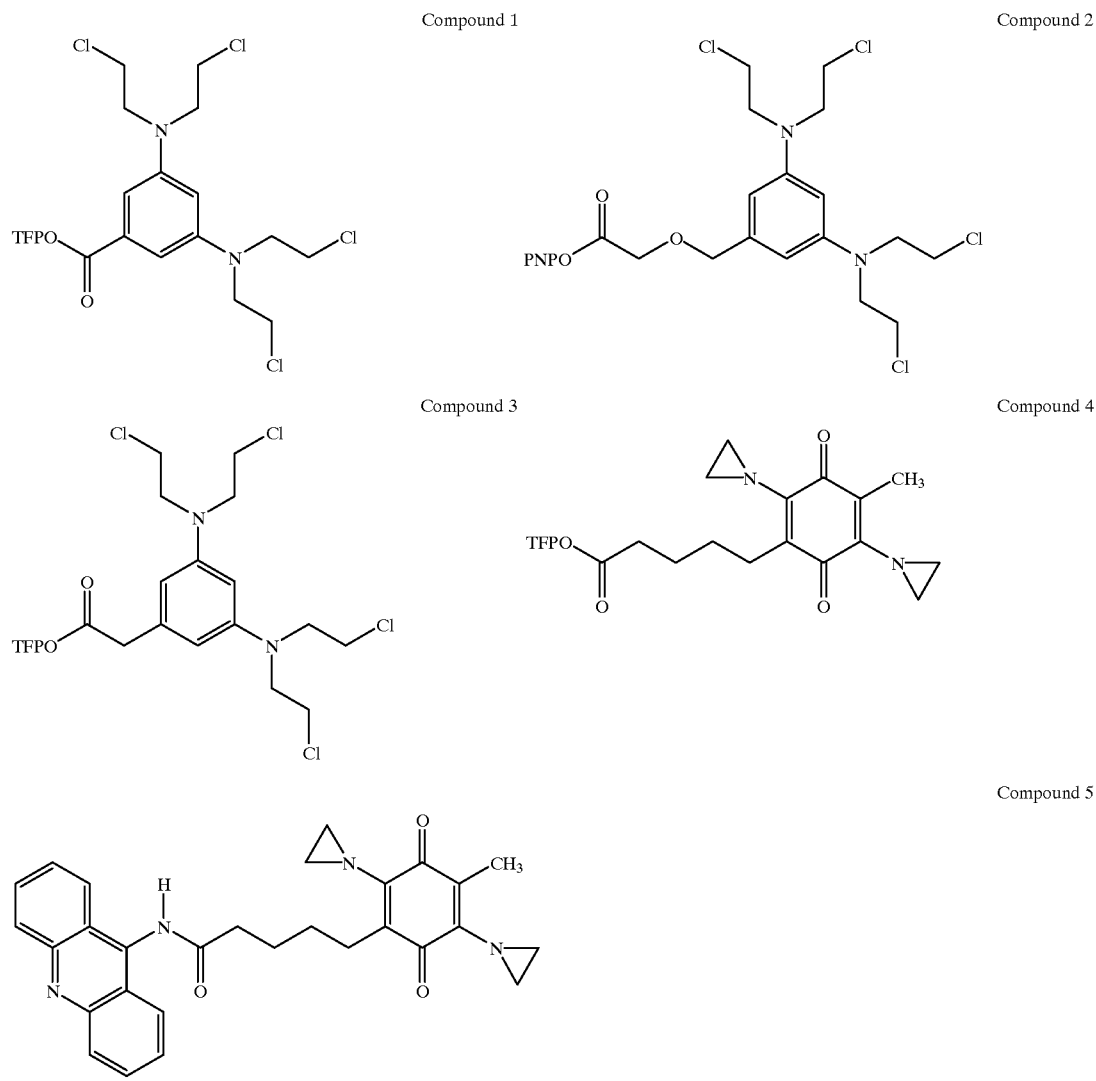

Compound 6

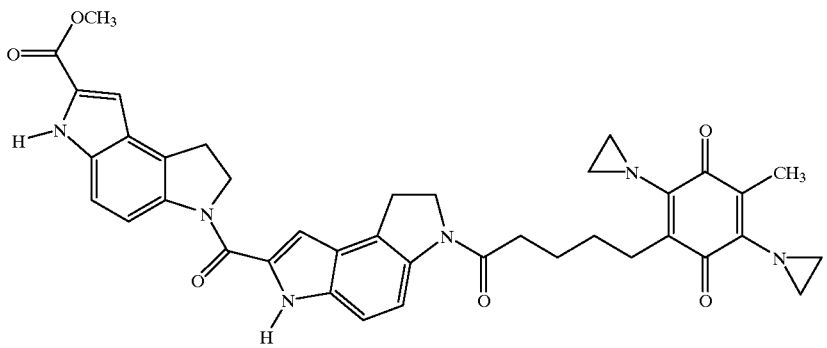

The ODN of SEQUENCE ID. No. 1 is a 21-mer that terminates with a aminohexyl "tail" attached to its phosphate on its 5' end, and also has a hydroxy hexyl "tail" attached to the phosphate group on its 3' end. The ODN of SEQUENCE ID. No. 1 is shown below.

Sequence ID No. 1

The ODN of SEQUENCE ID No. 1 is reacted with the activated ester reagents shown by formulas (7) through (11) to provide the ODN cross linker conjugates of SEQUENCE ID Nos. 2 through 6. As it should be readily apparent from the foregoing description, the nucleotide sequence and the 3' "tail" is exactly the same in each of the ODNs of SEQUENCE ID Nos. 1 through 6. Each of the ODNs of SEQUENCE ID Nos. 1 through 6 also has an aminohexyl tail. The difference among these ODNs is that the ODN of SEQUENCE ID No. 1 has no cross-linking functionality, and the remaining ODNs of SEQUENCE ID Nos. 2 through 6 have the cross linking and SPACER moieties shown in formulas (7) through (11) covalently attached to the amino group at their 5' hexylamine ends, respectively. This is indicated below

Sequence ID Nos. 2–6 wherein the structures of the ODNs of SEQUENCE ID Nos. 2–6 $R_5$ represents the crosslinking functionality and SPACER combinations shown in Formulas (7) through (11) respectively, that is the radicals shown in the structures of the reagents of Formulas (7) through (11) without the tetrafluorophenyloxy or para-nitrophenyloxy ($R_4$) moiety. The ODN of SEQUENCE ID No. 6 however is not within the scope of the invention because there is only one "nitrogen mustard" (di(chloroethyl)amino group) attached to the phenyl group.

SEQUENCE ID No. 7 is a double stranded 65-mer that is a "homopurine run-containing" fragment of the human DQβ1 *0302 allele. (Inheritance of this allele predisposes individuals to insulin-dependent diabetes mellitus.). The 65-mer used in the experiments pertaining to this invention was made synthetically. The G bases that are alkylated as a result of the cross-linking experiments with the ODNs of SEQUENCE ID Nos. 2 through 6 are underlined.

5'-CTACAGGCTTTAGCCTGGAAGAGAAG-
GAGAGAGGAGAGGAAAGAGGA
GACAAAGTGTACATTTAC

3'-GATGTCCGAAATCGGACCTTCTCTTC-
CTCTCTCCTCTCCTTTCTCCTCTGTTTCACATGTAAATG

Sequence ID No. 7

Cross-Linking and Related Experiments

Reaction of ODN-cross-linker conjugates with model nucleophiles:

To quantitate the relative reactivity of the nitrogen mustard ((di(chloroethyl)amino group) containing ODN-conjugates the ODNs of SEQUENCE ID Nos. 2, 3, and 4 were reacted with a model nucleophile (sodium thiosulfate) and degradation of starting material was measured over time using a reverse-phase HPLC assay. The half-life for reaction ($t_{1/2}$) at 37° C. was determined from data obtained in the HPLC assay, and the results are shown in Table 1. The relative reactivity of ODNs of SEQUENCE ID Nos 2, 3 and 4 are as predicted on the basis that electron donation by a substituent, including the LINKER, results in greater reactivity towards a nucleophile and therefore shorter half-life ($t_{1/2}$).

TABLE 1

| ODN, SEQUENCE ID No. | Reactivity ($t_{1/2}$) |
|---|---|
| 1 | not applicable |
| 2 | 140 min |
| 3 | 58 min |
| 4 | 26 min |
| 5 | >12 hours |
| 5 | <3.5 hours |
| (after reduction to hydroquinone) | |

The reactivity of the ODN-diaziridinylquinone conjugate of SEQUENCE ID No. 5 in aqueous thiosulfate solution was also measured using the same HPLC assay. Surprisingly, the ODN-diaziridinylquinone conjugate of SEQUENCE ID No. 5 was relatively unreactive with nucleophiles in solution. In aqueous buffer (pH 7.2) containing excess thiosulfate only 59% reaction was observed after 7 days at room temperature. In aqueous buffer (pH 7.2) without thiosulfate, only 24% reaction was observed after 7 days at room temperature. However, when treated with a reducing agent (sodium dithionite), the reactivity of the ODN of SEQUENCE ID No. 5 increased. After 3.5 hours at room temperature in thiosulfate solution a complex mixture of degradation products was observed with only 2% of the hydroquinone form of ODN-conjugate of SEQUENCE ID No. 5 remaining.

Sequence Specific DNA Alkylation by Triplex Forming ODN-conjugates of SEQUENCE ID Nos. 2 through 6

Sequence specific alkylation of the synthetic 65-mer ds DNA target of SEQUENCE ID No. 7 with the ODN-cross-linker conjugates of SEQUENCE ID Nos. 2 through 6 was studied in kinetic experiments. In these experiments either the purine or the pyrimidine rich strand of the ds ODN of SEQUENCE ID No. 7 was 5'-labeled with $^{32}$P. The hybridization buffers were identical to those used for the HPLC studies except for the presence of spermine and coralyne for triplex formation. After incubating the labeled dsDNA of SEQUENCE ID No. 7 with 100 fold excess of the ODN of interest (SEQUENCE ID Nos. 2–6, as applicable) at 37° C. for various periods of time, the extent of interstrand (bis) crosslinking and of single strand (mono) alkylation was measured by denaturing gel electrophoresis. After visualizing the radioactive bands by autoradiography, bis-crosslinking was observed as slow moving bands, mono alkylation of the labeled DNA strand was observed as intermediate mobility bands, and unmodified target strands were observed as fast moving bands. Quantitative kinetics studies were conducted using ds DNA of SEQUENCE ID No. 7 prepared from the 5'-$^{32}$P labeled strand containing the homopurine run. The extent of mono and bis DNA alkylation by the ODN-cross-linker conjugates of SEQUENCE ID Nos. 2–6 under various conditions is summarized in Table 2.

TABLE 2

| ODN Sequence ID No. | Reaction Time[a] | Labeled Strand | % Mono-alkylation | % Bis-alkylation |
|---|---|---|---|---|
| 2 | 10 h | pu[b] | 31 | 20 |
|   |      | py   | 6  | 21 |
| 3 | 20 h | pu   | 32 | 28 |
|   |      | py   | 3  | 24 |
| 4 | 6 h  | pu   | 28 | 52 |
|   |      | py   | 3  | 49 |
| 5 (pH 6.2) | 6 h | pu | 37 | 43 |
|            |     | py | 3  | 34 |
| 5 (pH 7.2) | 6 h | pu | 46 | 26 |
|            |     | py | 2  | 18 |
| 6 | 6 h | pu | 48 | trace |
|   |     | py | trace | 0 |

[a]Table 2 indicates the time at which the incubation at 37° C. was stopped and the mixture analyzed for products alkylated in that time
[b]pu stands for purine rich strand, py stands for pyrimidine rich strand The results summarized in Table 2 show that the triplex forming ODN-cross-linker conjugates (SEQUENCE ID Nos. 2–5) within the scope of the invention efficiently cross-link with both strands of the complementary DNA. In contrast with the ODN-cross-linker conjugates of the invention, the ODN-cross-linker conjugate containing only a single "nitrogen mustard" (di(chloroethyl)amino group) resulted only in a trace of cross-linking with both strands, although separate sequencing experiments showed that the site of alkylation with the ODN of SEQUENCE ID No. 6 is at a G base directly 3' of the triplex binding region.

Spontaneous de-purination and DNA strand cleavage were also observed upon prolonged incubation of the ODN of SEQUENCE ID No. 7 with the ODN-cross-linker conjugates of the invention. Heating the alkylated (cross-linked) DNA products in the presence of mild base (piperidine) gave quantitative, sequence specific DNA cleavage. This is an advantage for in vitro gene mapping experiments since interstrand DNA cross-linking events are converted to sequence specific double strand breaks. In this regard the cross-linking (bis-alkylating) triplex forming ODN-cross-linker conjugates of the invention can be viewed as mimics of restriction enzymes.

Experimental Section

Caution: Activated esters of the DNA alkylating agents are potentially toxic and should be handled with great care. DMSO solutions of these compounds are especially hazardous and disposable nitrile gloves or better protective devices should be used for these operations.

General: $^1$H and $^{13}$C NMR spectra were run on a Varian Gemini 300 MHz spectrometer. Elemental analyses were performed by Quantitative Techonologies Inc. (Boundbrook, N.J.). Melting points were determined on a Mel-Temp melting point apparatus in open capillary tubes and are uncorrected. All air and water sensitive reactions were carried out under a slight positive pressure of argon. Flash chromatography was performed on 230–400 mesh silica gel. Analytical thin-layer chromatography was carried out on EM Science $F_{254}$ aluminum backed, fluorescent indicator plates. 2,3,5,6-Tetrafluorophenyl trifluoroacetate (TFP-TFA) was prepared as described earlier by Gamper et al. (1993) Nucleic Acid Research 21, 145–150, incorporated herein by reference. 0.1 M Triethylammonium bicarbonate (TEAB) and 0.1 M tributylammonium bicarbonate (TBAB) were prepared by sparging a heterogeneous mixture of the appropriate amine with $CO_2$ until the organic layer disappeared.

Synthesis of 2,3,5,6 Tetrafluorophenyl (TFP) Ester, Compound 1

The scheme for preparation of Compound 1 is shown in Reaction Scheme 1.

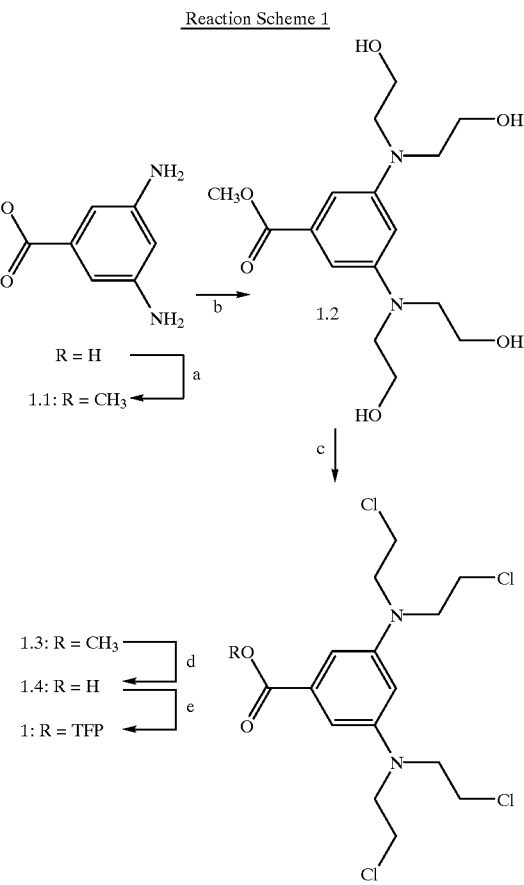

Reagents: (a) $CH_3OH$, HCl; (b) ethylene oxide; (c) $POCl_3$, N,N-dimethylacetamide; (d) LiOH, $CH_3OH$; (e) 2, 3, 5, 6-tetrafluorophenyl trifluoroacetate.

Methyl 3,5-diaminobenzoate (1.1)

HCl gas was bubbled through a solution of 3,5-diaminobenzoic acid (4.5 g, 30 mmol) in 250 mL of dry methanol. The bubbling was continued for about 10 minutes until no starting material was detected by thin layer chromatography (TLC). The resulting hot solution was cooled and concentrated in vacuo. The residue was partitioned between $CH_2Cl_2$ and saturated $NaHCO_3$. The organic phase was washed with brine and dried over $Na_2SO_4$. Concentration in vacuo afforded the title compound as a pale pink solid (4.0 g, 81%): mp 131–132° C.; $^1$H NMR (CDCl$_3$) δ 6.78 (d, J=2.1 Hz, 2H), 6.18 (d, J=2.1 Hz, 1H), 3.85 (s, 3H, CH$_3$), 3.65 (br s, 4H, NH$_2$); $^{13}$C NMR (CDCl$_3$) δ 167.45, 147.53, 132.08, 106.95, 105.68, 52.06. Anal. calcd. for $C_8H_{10}N_2O_2$: C, 57.82; H, 6.07; N, 16.86. Found: C, 57.54; H, 5.92; N, 16.64.

Methyl 3,5-[N,N,N',N'-tetrakis-(2-hydroxyethyl)] diaminobenzoate (1.2)

To an ice cold solution of 1.1 (4.0 g, 24 mmol) in a mixture of acetic acid (25 mL) and water (10 mL) was added ethylene oxide (13 mL, 290 mmol). The reaction mixture was placed in a water bath and stirred at ambient temperature for 48 hours. The reaction mixture was concentrated in vacuo to a viscous syrup. Residual solvent was removed by co-evaporation with acetonitrile. The resulting oil was suspended in acetonitrile and stirred for about 5 minutes before crystals started to form. Stirring was continued for another 30 minutes, the precipitate was collected by filtration and washed with acetonitrile. Drying in vacuo afforded 4.5 g (60%) of the title compound as an off white solid: mp 130–132° C.; $^1$H NMR (DMSO-d6) δ 6.57 (d, J=1.9 Hz, 2H), 6.63 (t, J=1.9 Hz, 1H), 4.80 (br s, 4H, OH), 3.78 (s, 3H, CH$_3$), 3.53 (t, J=6 Hz, 8H, CH$_2$O—), 3.40 (t, J=6 Hz, 8H, NCH$_2$); $^{13}$C NMR (DMSO-d6) δ 167.47, 148.86, 130.85, 100.33, 99.00, 58.16, 53.36, 51.90. Anal. calcd. for $C_{16}H_{26}N_2O_6$: C, 56.13; H, 7.65; N, 8.18. Found: C, 55.81; H, 7.32, N, 7.93.

Methyl 3,5-[N,N,N',N'-tetrakis-(2-chloroethyl)] diaminobenzoate (1.3)

To a stirred solution of 1.2 (2.0 g, 6.5 mmol) in 30 mL of dry N,N-dimethylacetamide was added dropwise POCl$_3$ (10 mL, 109 mmol). The resulting hot solution was stirred at 90° C. for 40 minutes, then cooled, poured over crushed ice and carefully (foaming) neutralized with saturated NaHCO$_3$. The mixture was extracted with ether, the organic phase was washed with water, brine and dried over Na$_2$SO$_4$. The crude product obtained after concentration was crystallized from 50% ethyl acetate in hexane to afford 1.7 g (65%) of the desired tetrakis-chloroethyl derivative 1.3 as pale yellow crystals: mp 103–104° C.; $^1$H NMR (CDCl$_3$) δ 6.81 (d, J=2.3 Hz, 2H), 6.17 (d, J=2.3 Hz, 1H), 3.80 (s, 3H, CH$_3$), 3.77 (m, 8H, CH$_2$Cl), 3.66 (m, 8H, NCH$_2$); $^{13}$C NMR (DMSO-d6) δ 167.50, 147.63, 132.55, 103.19, 100.24, 53.73, 52.34, 40.70. Anal. calcd. for $C_{16}H_{22}N_2O_2Cl_4$: C, 46.18; H, 5.33; N, 6.73. Found: C, 45.88; H, 5.06; N, 6.51.

3,5-[N,N,N',N'-Tetrakis-(2-chloroethyl)]diaminobenzoic acid (1.4)

To a solution of 1.3 (1.0 g, 2.5 mmol) in a mixture of methanol (10 mL) and CH$_2$Cl$_2$ (10 mL) was added 2M LiOH monohydrate in methanol (10 mL, 20 mmol). The solution was stirred for 40 hours at ambient temperature, then acetic acid (1.2 mL, 20 mmol) was added to neutralize the reaction. The solvents were removed by evaporation, and the residue was partitioned between CH$_2$Cl$_2$ and water. The organic phase was washed with brine and dried over Na$_2$SO$_4$. Evaporation of the solvent afforded a crystalline solid which was re-crystallized from ethyl acetate-hexane to give 0.68 g (70%) of the desired acid 1.4 as white needles: mp 156–158° C.; $^1$H NMR (CDCl$_3$) δ 6.89 (d, J=2.3 Hz, 2H), 6.23 (t, J=2.3 Hz, 1H), 3.79 (m, 8H, CH$_2$Cl), 3.68 (m, 8H, NCH$_2$); $^{13}$C NMR (CDCl$_3$) 172.20, 147.74, 131.51, 103.57, 100.88, 53.75, 40.65. Anal. calcd. for $C_{15}H_{20}N_2O_2Cl_4$: C, 44.80; H, 5.01; N, 6.97. Found: C, 45.03; H, 4.73; N, 6.77.

2,3,5,6-Tetrafluorophenyl 3,5-[N,N,N',N'-tetrakis-(2-chloroethyl)]diaminobenzoate (1).

To a solution of acid 1.4 (200 mg, 0.5 mmol) in 2 mL of dry CH$_2$Cl$_2$ were added triethylamine (0.22 mL, 1.6 mmol) and 2,3,5,6-tetrafluorophenyl trifluoroacetate (0.25 mL, 1.4 mmol). After being stirred for 1 hour, the mixture was applied onto a silica gel column (2×25 cm). Elution with hexane-ethyl acetate (4:1) followed by concentration of the proper fractions afforded the title product 1 as a white crystalline solid (0.25 g, 76%): mp 65–66° C.; $^1$H NMR (CDCl$_3$) δ 7.05 (m, 1H, TFP), 6.95 (d, J=2.3 Hz, 2H), 6.30 (t, J=2.3 Hz, 1H), 3.81 (m, 8H, CH$_2$Cl), 3.69 (m, 8H, NCH$_2$). Anal. calcd. for $C_{21}H_{20}N_2O_2Cl_4F_4$: C, 45.84; H, 3.66; N, 5.09. Found: C, 46.04; H, 3.52; N, 4.83.

Synthesis of para Nitrophenyl (PNP) Ester, Compound 2

The scheme for preparation of Compound 2 is shown in Reaction Scheme 2.

Reaction Scheme 2

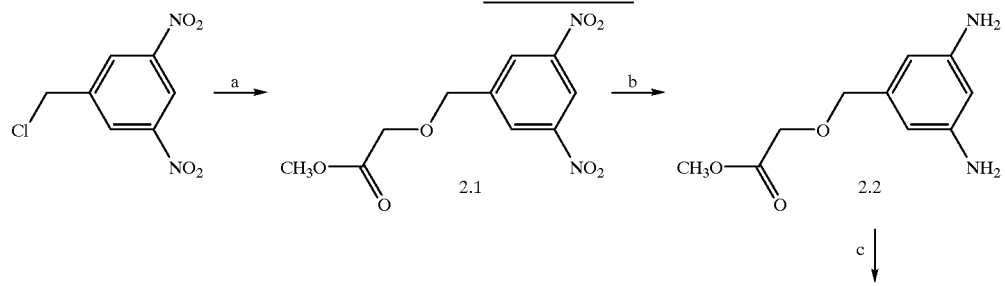

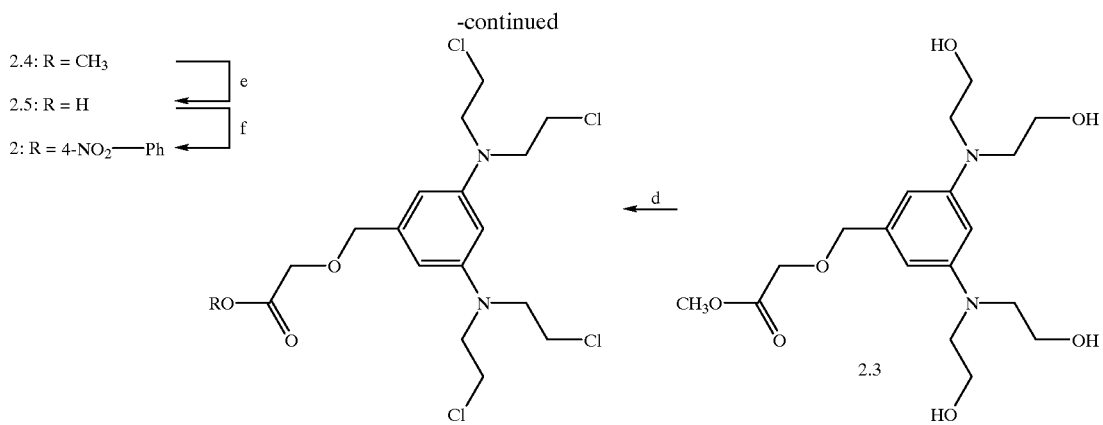

Reagents: (a) methyl glycolate, NaH; (b) SnCl$_2$/MeOH; (c) ethylene oxide; (d) POCl$_3$, N,N-dimethylacetamide; (e) LiOH, CH$_3$OH; (f) 4-nitrophenol, DCC.

Methyl 3,5-dinitrobenzoxyacetate (2.1)

To a solution of methyl glycolate (10 mL, 130 mmol) in THF (50 mL) at −70° C. (acetone-dry ice) was added in small portions, with stirring 60% NaH in oil (1.6 g, 111 mmol). To the resulting white suspension was added a solution of 3,5-dinitrobenzylchloride (5.0 g, 23 mmol). The reaction was allowed to warm to room temperature and acetic acid (2 mL) was added to quench excess NaH. The reaction mixture was concentrated and the residual tan oil was partitioned between water and CH$_2$Cl$_2$. The organic phase was washed with water and dried over Na$_2$SO$_4$. The crude product obtained after concentration was chromatographed on a silica gel column (4×25 cm) eluting with 33% ethyl acetate in hexane. Concentration of appropriate fractions followed by drying in vacuo gave 5.1 g (93%) of the desired product 2.1 as a pale yellow crystalline solid: $^1$H NMR (CDCl$_3$) δ 8.98 (s, 1H, C$_4$—H), 8.59 (s, 2H, C$_2$—H), 4.85 (s, 2H, CH$_2$), 4.29 (s, 2H, CH$_2$), 3.81 (s, 3H, CH$_3$); $^{13}$C NMR (CDCl$_3$) δ 170.16, 148.58, 142.33, 127.30, 118.15, 71.10, 68.07, 52.18.

Methyl 3,5-diaminobenzoxyacetate (2.2)

A mixture of 2.1 (5.0 g, 18.5 mmol), SnCl$_2$ dihydrate (48.0 g, 212.7 mmol) in 60 mL of methanol was refluxed for 40 minutes. The resulting dark solution was cooled (ice bath) and cautiously neutralized by adding saturated NaHCO$_3$. The solid precipitate was filtered off and washed with methanol and CH$_2$Cl$_2$ until no product was found (by TLC) in the washings. The filtrate and washings were combined and evaporated in vacuo to give crude diamine 2.2. Chromatography on a silica gel column (4.5×20 cm) eluting with ethyl acetate afforded the title compound as a yellow oil (2.5 g, 64%), which slowly crystallized upon drying in vacuo: $^1$H NMR (CDCl$_3$) δ 6.11 (d, J=2 Hz, 1H, C$_4$—H), 5.96 (t, J=2 Hz, 2H, C$_2$—H), 4.44 (s, 2H, CH$_2$), 4.07 (s, 2H, CH$_2$), 3.75 (s, 3H, CH$_3$), 3.59 (br s, 4H, NH$_2$); $^{13}$C NMR (CDCl$_3$) δ 170.96, 147.78, 139.33, 105.51, 101.41, 73.31, 66.85, 51.89.

Methyl 3,5-[N,N,N',N'-tetrakis-(2-hydroxyethyl)] diaminobenzoxyacetate (2.3)

To an ice cold solution of 2.2 (2.4 g, 11.4 mmol) in a mixture of acetic acid (15 mL) and water (7 mL) was added ethylene oxide (10 mL, 223 mmol). The reaction mixture was placed in a water bath and stirred at ambient temperature for 24 hours. The reaction mixture was concentrated in vacuo to an oil. Chromatography on a silica gel column (4.5×20 cm) eluting with 10% methanol in CH$_2$Cl$_2$ followed by concentration of the proper fractions afforded 2.3 (3.7 g, 84%) as a tan syrup: $^1$H NMR (CDCl$_3$) δ 6.07 (s, 2H, C$_2$—H), 6.01 (s, 1H, C$_4$—H), 4.45 (s, 2H, CH$_2$), 4.07 (s, 2H, CH$_2$), 4.0 (br s, 4H, OH), 3.73 (m, 11H, s-CH$_3$=m-CH$_2$), 3.44 (m, 8H, CH$_2$); $^{13}$C NMR (CDCl$_3$) δ 171.13, 149.35, 138.49, 101.86, 97.74, 74.34, 66.95, 63.61, 55.33, 51.98.

Methyl 3,5-[N,N,N',N'-tetrakis-(2-chloroethyl)] diaminobenzoxyacetate (2.4)

To a stirred solution of 2.3 (3.4 g, 8.8 mmol) in 40 mL of dry N,N-dimethylacetamide was added dropwise POCl$_3$ (10 mL, 109 mmol). The resulting hot solution was stirred at 90° C. for 40 min, then cooled, diluted with CH$_2$Cl$_2$, poured over crushed ice (~200 g) and cautiously (foaming) neutralized with saturated NaHCO$_3$. The organic phase was washed with water, brine and dried over Na$_2$SO$_4$. The crude product (oil) obtained after concentration was chromatographed on a silica gel column (4.5×20 cm) eluting with 33% ethyl acetate in hexane. The fractions containing pure product were pooled and concentrated to afford the title compound 2.4 as a colorless syrup (2.2 g, 55%): $^1$H NMR (CDCl$_3$) δ 6.14 (d, J=2.2 Hz, 2H, C$_2$—H), 5.91 (t, J=2.1 Hz, 1H, C$_4$—H), 4.53(s, 2H, CH$_2$), 4.12 (s, 2H, CH$_2$), 3.78 (s, 3H, CH$_3$), 3.73 (m, 8H, CH$_2$), 3.64 (m, 8H, CH$_2$); $^{13}$C NMR (DMSO-d6) δ 170.82, 147.83, 139.99, 101.62, 95.72, 73.95, 67.15, 53.71, 51.98, 40.70.

N,N,N',N'-3,5-[Tetrakis-(2-chloroethyl)] diaminobenzoxyacetic acid (2.5)

To an ice cold solution of 2.4 (2.1 g, 4.56 mmol) in a mixture of methanol (10 mL) and CH$_2$Cl$_2$ (10 mL) was added 2M LiOH monohydrate in methanol (10 mL, 20 mmol). The solution was stirred for 2 hours at 0° C., then 1M HCl (21 mL) was added to neutralize the reaction. The solvents were removed by evaporation, and the residue was partitioned between ether and water. The organic phase was washed with brine and dried over Na$_2$SO$_4$. Evaporation of the solvent afforded the acid 2.5 as a crystalline solid (1.9 g, 93%) $^1$H NMR (CDCl$_3$) δ 6.13 (d, J=2 Hz, 2H, C$_2$—H), 5.92 (t, J=2 Hz, 1H, C$_4$—H), 4.55 (s, 2H, CH$_2$), 4.17 (s, 2H, CH$_2$), 3.73 (m, 8H, CH$_2$), 3.66 (m, 8H, NCH$_2$); $^{13}$C NMR CDCl$_3$) δ 174.53, 147.91, 139.48, 101.65, 95.87, 74.15, 66.63, 53.67, 40.70.

4-Nitrophenyl 3,5-[N,N,N',N'-tetrakis-(2-chloroethyl)] diaminobenzoxyacetate (2)

To a solution of acid 2.5 (105 mg, 0.23 mmol) in 5 mL of dry ether were added 4-nitrophenol (60 mg, 0.43 mmol) and N,N'-dicyclohexylcarbodiimide (100, 0.48 mmol). After being stirred for 3 hours, N,N'-dicyclohexylurea was removed by filtration. The concentrated filtrate was applied onto a silica gel column (2×25 cm). Elution with hexane-ethyl acetate (3:1) followed by concentration of the proper fractions afforded the title product 2 as a pale yellow syrup (70 mg, 54%): $^1$H NMR (CDCl$_3$) δ.

Synthesis of 2,3,5,6 Tetrafluorophenyl (TFP) Ester, Compound 3

The scheme for preparation of Compound 3 is shown in Reaction Scheme 3.

(10 mL, 109 mmol). The resulting hot solution was stirred at 90° C. for 40 minutes, then cooled, diluted with CH$_2$Cl$_2$, poured over crushed ice (~200 g) and cautiously (foaming) neutralized with saturated NaHCO$_3$. The organic phase was washed with water, brine and dried over Na$_2$SO$_4$. The crude product (red oil) obtained after concentration was chromatographed on a silica gel column (4.5×20 cm) eluting with 25% ethyl acetate in hexane. The fractions containing pure

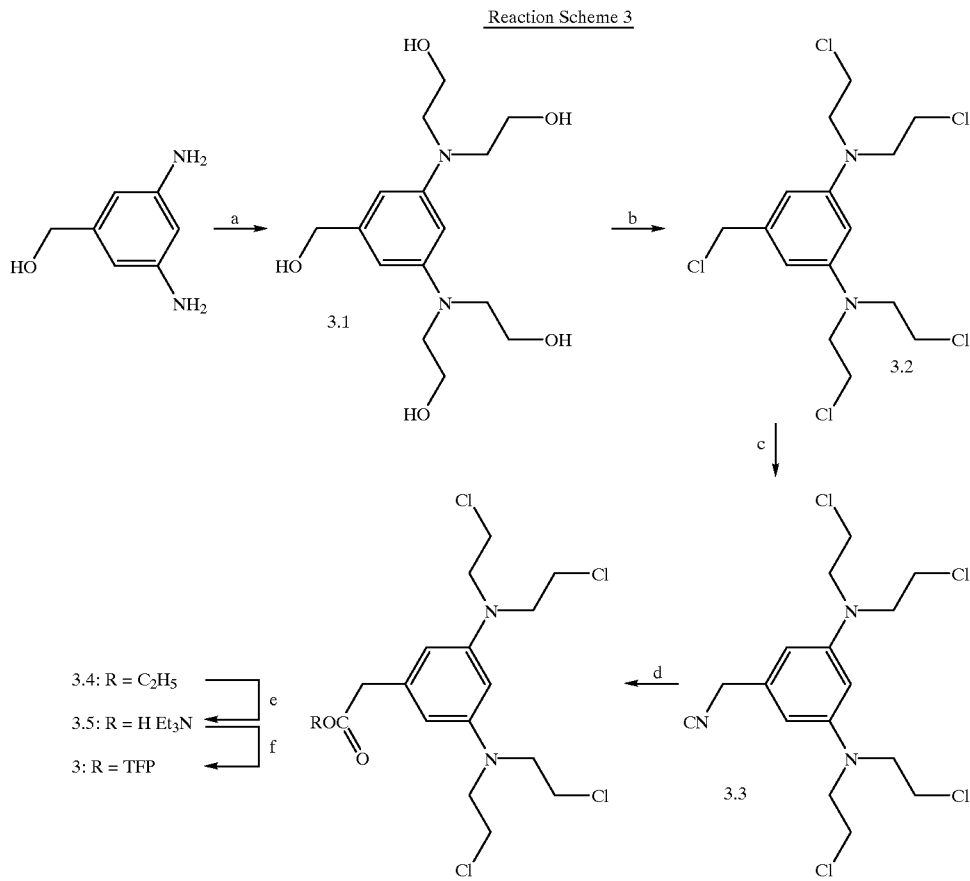

Reaction Scheme 3

Reagents: (a) ethylene oxide, acetic acid, water; (b) POCl$_3$, DMA; (c) KCN, 18-crown-6; (d) HCl/ethanol; (e) LiOH, CH$_3$OH; (f) TFP-TFA 3,5-[N,N,N',N'-Tetrakis-(2-hydroxyethyl)]diaminobenzyl alcohol (3.1)

To an ice cold solution of 3,5-diaminobenzyl alcohol dihydrochloride (5.0 g, 23.7 mmol) in 20 mL of water was added triethylamine (3.35 mL, 24 mmol) followed by acetic acid (24 mL). The resulting tan solution was cooled on ice, ethylene oxide (20 mL, 450 mmol) was added and the stoppered solution was kept at ambient temperature for 10 hours. The reaction mixture was concentrated to afford crude 3.1 as a tan solid. The solid was washed with a hot mixture of acetonitrile and methanol containing triethylamine (3 mL). Drying in vacuo afforded 4.1 g (55%) of analytically pure 3.1 as a pink solid: $^1$H NMR (DMSO-d6) δ 5.94 (s, 2H, C$_2$—H), 5.79 (s, 1H, C$_4$—H), 4.90 (t, 5 Hz, 1H, OH), 4.72 (br s, 4H, OH), 4.30 (d, J=5 Hz, 1H, benzyl CH$_2$), 3.51 (m, 8H, CH$_2$), 3.35 (m, 8H, CH$_2$); $^{13}$C NMR (DMSO-d6) δ 148.65, 143.65, 98.45, 93.77, 64.09, 58.40, 53.54.

3,5-[N,N,N',N'-Tetrakis-(2-chloroethyl)]diaminobenzyl chloride (3.2)

To a stirred solution of 3.1 (3.95 g, 12.6 mmol) in 40 mL of dry N,N-dimethylacetamide was added dropwise POCl$_3$ product were pooled and concentrated to afford the title compound 3.2 as a tan syrup (4.4 g, 86%): $^1$H NMR (CDCl$_3$) δ 6.15 (s, 2H, C$_2$—H), 5.93 (s, 1H, C$_4$—H), 4.49 (s, 2H, benzyl CH$_2$), 3.74 (m, 8H, CH$_2$), 3.65 (m, 8H, CH$_2$); $^{13}$C NMR (CDCl$_3$) δ 147.92, 140.28, 102.26, 95.95, 53.70, 47.19, 40.61.

3,5-[N,N,N',N'-Tetrakis-(2-chloroethyl)]diaminobenzonitrile (3.3)

To a solution of KCN (3.35 g, 51.5 mmol) and 18-crown-6 (15.0 g, 56.8 mmol) in 70 mL of dry CH$_2$Cl$_2$ was added a solution of 3.2 (4.2 g, 10.3 mmol) in 10 mL of dry CH$_2$Cl$_2$. The solution was kept at ambient temperature for 2 hours, then diluted with CH$_2$Cl$_2$ (~150 mL), washed with water (4×200 mL) and dried over Na$_2$SO$_4$. The reaction mixture was concentrated in vacuo to give a yellow oil. Chromatography on a silica gel column (4.5×20 cm) eluting with 20% ethyl acetate in hexane followed by concentration of the proper fractions afforded 3.3 (3.2 g, 78 %) as a colorless syrup: $^1$H NMR (CDCl$_3$) δ 6.05 (d, J=2 Hz, 2H, C$_2$—H), 5.92 (t, J=2 Hz, 1H, C$_4$—H), 3.72 (m, 8H, CH$_2$), 3.67 (m, 8H, CH$_2$), 3.65 (s, CH$_2$ partially obscured by 3.67 ppm multiplet).

Ethyl 3,5-[N,N,N',N'-tetrakis-(2-chloroethyl)]diaminophenylacetate (3.4)

HCl gas was bubbled through a suspension of nitrile 3.3 (3.1 g) in 50 mL of 95% ethanol for ~5 minutes with cooling in an ice bath. The resultant solution was kept at ambient temperature for 3 hours, TLC analysis (33% ethyl acetate in hexane) showed two major products: ethyl ester (3.4) with $R_f$ 0.9 and amide $R_f$ 0.15. The products were separated by flash chromatography on a silica gel column (4.5×25 cm) eluting with 33% ethyl acetate in hexane. The ethyl ester 3.4 (faster eluting product) was obtained as a colorless syrup (1.1 g, 32%): $^1$H NMR (CDCl$_3$) δ 6.06 (d, J=2 Hz, 2H, C$_2$—H), 5.88 (t, J=2 Hz, 1H, C$_4$—H), 3.72 (m, 8H, CH$_2$), 3.62 (m, 8H, CH$_2$), 3.51 (s, 2H, CH$_2$).

3,5-[N,N,N',N'-Tetrakis-(2-chloroethyl)]diaminophenylacetic acid (3.5)

To a solution of 3.4 (1.1 g, 2.5 mmol) in a mixture of methanol (5 mL) and CH$_2$Cl$_2$ (5 mL) was added 2M LiOH monohydrate in methanol (5 mL, 20 mmol). The resulting emulsion was stirred for 5 minutes to give a clear solution, the reaction was stirred at 50° C. for another 45 minutes, then cooled and neutralized with acetic acid (0.65 mL). The solvents were removed by evaporation, and the residue was partitioned between ether and water. The organic phase was washed with brine and dried over Na$_2$SO$_4$. Evaporation of the solvent afforded crude acid 3.5 as a pink syrup. It was purified by flash chromatography on a silica gel column (4.5×15 cm) eluting with 5%/2% triethylamine in CH$_2$Cl$_2$. The title product (3.5) was obtained as a triethylammonium salt (1.1 g, 85%) after evaporation of the solvent and drying in vacuo: $^1$H NMR (CDCl$_3$) δ 6.12 (d, J=2 Hz, 2H, C$_2$—H), 5.80 (t, J=2 Hz, 1H, C$_4$—H), 3.68 (m, 8H, CH$_2$), 3.62 (m, 8H, CH$_2$), 3.45 (m, 2H, CH$_2$), 2.99 (q, 6H, CH$_2$ from Et$_3$N), 1.21 (t, 9H, CH$_3$ from Et$_3$N).

2,3,5,6-Tetrafluorophenyl 3,5-[N,N,N',N'-tetrakis-(2-chloroethyl)]diaminophenylacetate (3)

To a solution of acid 3.5 (1.0 g, 1.93 mmol) in 10 mL of dry CH$_2$Cl$_2$ were added triethylamine (0.15 mL, 1.1 mmol) and 2,3,5,6-tetrafluorophenyl trifluoroacetate (0.6 mL, 3.4 mmol). After being stirred for 1 hour, the mixture was applied onto a silica gel column (4.5×20 cm). Elution with hexane-ethyl acetate (4:1) followed by concentration of the proper fractions afforded the title product 3 as a white crystalline solid (0.9 g, 83%): mp 63–64° C.; $^1$H NMR (CDCl$_3$) δ; 7.01 (m, 1H, TFP), 6.11 (d, J=2 Hz, 2H, C$_2$—H), 5.93 (t, J=2 Hz, 1H, C$_4$—H), 3.88 (s, 2H, CH$_2$), 3.72 (m, 8H, CH$_2$), 3.65 (m, 8H, CH$_2$).

Synthesis of 2,3,5,6 Tetrafluorophenyl (TFP) Ester, Compound 4

The scheme for preparation of Compound 4 is shown in Reaction Scheme 4.

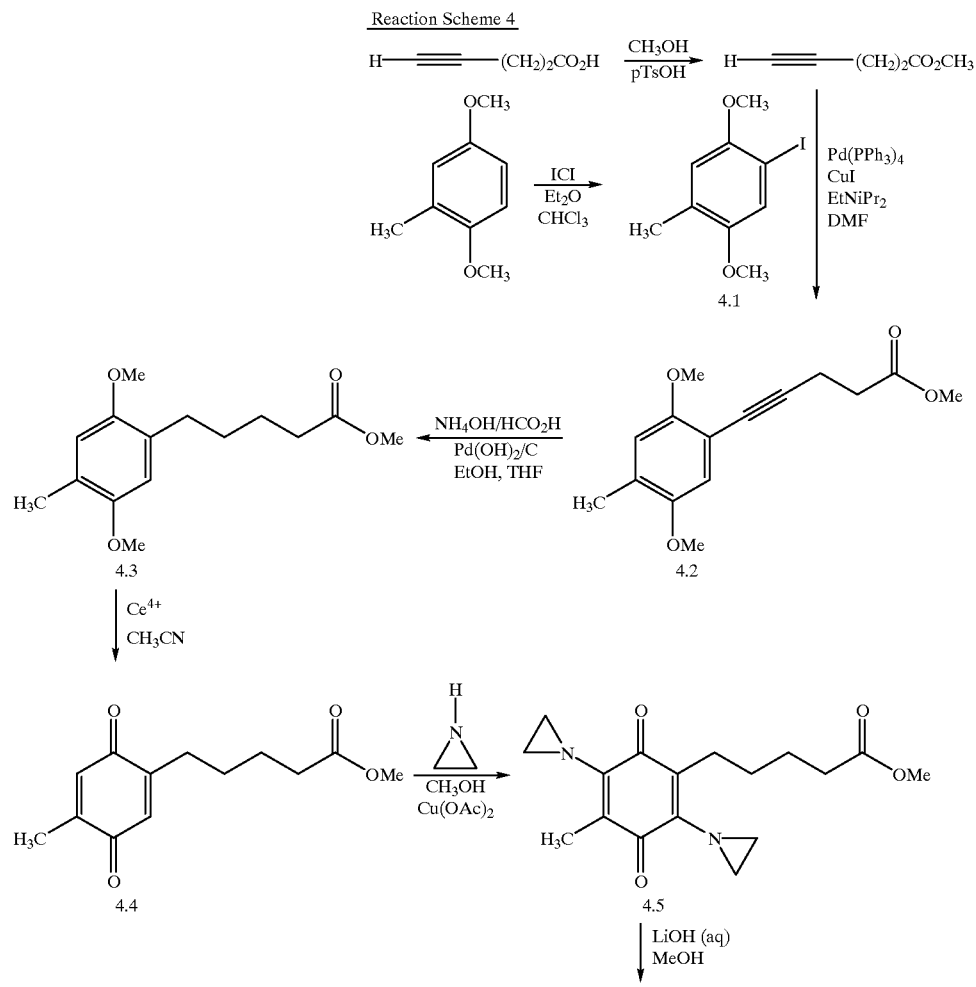

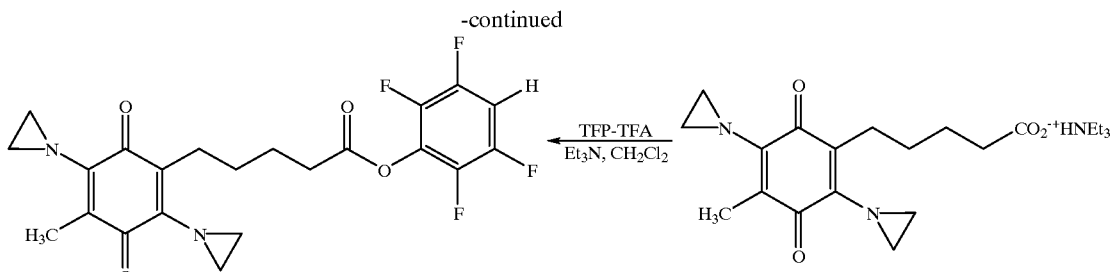

4-Iodo-2,5, dimethoxytoluene (4.1)

To a stirred solution of 7.19 grams (47 mmol)of 2,5 dimethoxytoluene (Aldrich) in 50 ml of dry ethyl ether, a solution of 7.66 g (47 mmol) of iodine monochloride in 20 ml of chloroform was added dropwise, using a dropping funnel, over about 30 minutes. Stirring was continued for another 3 hours. Then 250 mL of ethyl ether was added and the mixture was transferred to a separatory funnel. Then 200 ml of 10% sodium thiosulfate with 6 g. sodium bicarbonate was added to the funnel and the mixture was shaken, with frequent venting, until the iodine color was gone. The organic layer was washed again with a similar portion of the thiosulfate solution and dried over sodium sulfate, then evaporated. The resulting white material was dissolved in 100 ml of boiling methanol. Then the solution was cooled overnight in a freezer. The resulting white crystals were filtered and washed with 75% chilled methanol, then dried. m.p. 81–82° C., yield 9.283 g. (71%). TLC (methylene chloride) $R_f$=0.87 (0.83 for starting material). $^1$H NMR (CDCl$_3$), δ: 7.18 (s, 1H); 6.68 (s, 1H); 3.82 (s, 3H) 3.78 (s, 3H); 2.19 (s, 3H).

4-Pentynoic acid, 5-(2,5-dimethoxy-4-methylphenyl)-, methyl ester (4.2)

To 3.88 g. (14.0 mmol) of the aryl iodide 4.1 and 1.88 g methyl pentynoate (16.7 mmol) in 50 mL of dry DMF was added 0.277 g. (1.45 mmol) of cuprous iodide and 0.80 g. (0.69 mmol) of tetrakis (triphenylphosphine palladium (0) (Lancaster). The flask was flushed with argon and sealed with a septum, and 3.6 mL of N,N-diisopropylethylamine was added to the flask. After stirring overnight, TLC showed a trace of unreacted starting material. The solution was evaporated and the residue was purified by flash chromatography (5×40 cm silica) using a gradient of 1:1 hexanes-methylene chloride to 100% methylene chloride. Evaporation gave a dark brown solid. Despite good NMR purity, a second silica gel column was run using an eluent of 4:1 hexanes-ethyl acetate to eliminate color. Appropriate fractions were collected and evaporated to give 1.88 g (51% yield) of the desired product 4.2 as an off-white solid: mp=66–67 C; TLC (2:1 hexanes-ethyl acetate) Rf=0.63; $^1$H NMR (CDCl$_3$), 6.77 (s, 1H), 6.62 (s, 1H), 3.78 (s, 3H), 3.73 (s, 3H), 3.67 (s, 3H), 2.75 (t, 2H, J=6.3 Hz), 2.63 (t, 2H, J=6.3 Hz), 2.16 (s, 3H). Anal. Calcd for C$_{15}$H$_{18}$O$_4$: C, 68.69; H: 6.92. Found: C: 68.59; H: 6.53.

Benzenepentanoic acid, 2,5-dimethoxy-4-methyl-, methyl ester (4.3)

To 186 mg of 10% palladium on carbon) was added 3.7 mL of ethanol and 3 drops of formic acid. The mixture was warmed enough to produce slight effervescence. After 30 minutes, this mixture was degassed and saturated with hydrogen by several cycles of evacuating and hydrogen flushing and left under a balloon of hydrogen. In a separate flask, 3.7 mL of 4M aqueous triethylammonium formate (pH 6.5) was mixed with an equal volume of ethanol and deoxygenated similarly, then added to the solution in the flask. A solution of 1.12 g (4.27 mmol) of the alkyne (4.2) in 7.5 mL dry THF and 3.7 mL ethanol was introduced into the hydrogenation flask. After stirring at room temperature 19 hours, TLC showed no residual starting material. The mixture was filtered through diatomaceous earth in a sintered glass funnel, and the solids were rinsed with a few mL of ethanol. The filtrate was concentrated in vacuo and the residue was partitioned between 3% sodium bicarbonate and ethyl acetate. The organic layer was evaporated to dryness to give 1.08 g (96%) of 4.3 as a colorless liquid. TLC (2:1 hexanes-ethyl acetate) $R_f$=0.80. $^1$H NMR (CDCl$_3$) 6.67 (s, 1H), 6.64 (s, 1H); 3.80 (s, 3H), 3.77 (s, 3H), 3.67 (s, 3H), 2.60 (t, 2H, J=7.7 Hz), 2.36 (t, 2H, J=7.1 Hz), 1.8–1.6 (m, 4H). Anal. Calcd for C$_{15}$H$_{22}$O$_4$: C, 67.65; H, 8.33. Found: C, 67.39; H, 8.10.

1,4-Cyclohexadiene-1-pentanoic acid, 4-methyl-3,6-dioxo-, methyl ester (4.4)

To a solution of 1.08 g. (4.07 mmol) of 4.3 in 20 mL of acetonitrile was added a solution of 4.69 g. (8.56 mmol) of ceric ammonium nitrate in 10 mL water. The aqueous solution was added to the stirred organic solution, dropwise, with stirring, until the transient green color that occurs during addition was no longer visible. After stirring for 45 minutes, the solvents were removed and the residue was partitioned between water and ethyl acetate. The organic layer was dried over sodium sulfate and evaporated to dryness. 5 mL of ethyl acetate and 5 mL of hexanes were added to dissolve the residual crude product. It was purified by flash chromatography gel (5×50 cm silica) using 4:1 mixture hexanes-ethyl acetate. Evaporation of the yellow band gave the desired compound 4.4 with slight contamination. The solid was dissolved in 12 mL of boiling methanol and 6 mL of hot water was added. The resulting crystals were filtered and washed with a few mL of cold 50% methanol and vacuum dried to give 0.69 g. (71% yield) of 4.4 as yellow crystals: mp=46–48° C.; TLC (4:1 hexanes-ethyl acetate) $R_f$=0.45. $^1$H NMR (CDCl$_3$) 6.59 (s, 1H), 6.55 (s, 1H), 3.67 (s, 3 H), 2.43 (t, 2H, J=7.4 Hz), 2.35 (t, 2H, J=7.1 Hz), 2.04 (s, 3H), 1.69 (m, 2H), 1.54 (m, 2H). Anal. Calcd for C$_{13}$H$_{16}$O$_4$: C, 66.09; H, 6.83; 0, 27.09. Found: C, 66.12; H, 6.75.

1,4-Cyclohexadiene-1-pentanoic acid, 2,5-bis(1-aziridinyl)-4-methyl-3,6-dioxo-, methyl ester (4.5)

To a stirred solution of 0.686 g. (2.90 mmol) of 4.4 in 18.8 mL of methanol was added 105 mg. (0.594 mmol) of cupric acetate. 1.53 mL (29.0 mmol) of ethylenimine was added, and an air filled balloon was placed over the neck of the flask, to provide a reservoir of oxygen while at the same time controlling evaporation of aziridine. Stirring was moderately fast (600 to 800 rpm). TLC of the heterogeneous mixture showed nearly complete reaction after 15 minutes. The mixture was evaporated and the residue was purified by flash chromatography (5×50 cm silica) using 2:1 hexanes-ethyl acetate (2% triethlamine). A red elution band was collected and evaporated to give 827 mg (90% yield) of 4.5 as orange-red crystals: mp=97–99° C. TLC (2:1-hexanes/ethyl acetate) $R_f$=0.33; 1H NMR, (CDCl$_3$) 3.66 (s, 3H), 2.53 (t, 2H, J=7.7 Hz), 2.35 (t, 2H, =7.4 Hz), 2.29 (s, 4H), 2.27 (s, 4H), 1.71 (m, 2 H), 1.53 m, 2H). Anal. Calcd for C$_{17}$H$_{22}$N$_2$O$_4$: C, 64.13; H, 6.96; N, 8.80; Found: C, 64.04; H, 6.85; N, 8.61.

1,4-Cyclohexadiene-1-pentanoic acid, 2,5-bis(1-aziridinyl)-4-methyl-3.6-dioxo-, triethylammonium salt (4.6)

To a solution of 1.01 g. (2.50 mmol) of 4.5 in 25 mL of methanol was added 4 mL of 1 N LiOH. The mixture was stirred at 50–60° C. for 4 hours, cooled to room temperature, and concentrated in vacuo. The residue was purified by flash chromatography (5×50 cm silica) using 19:1 methylene chloride-methanol (2% triethylamine). The product was eluted with a gradient containing up to 10% methanol. The major red band of elution was collected and evaporated to give 0.974 g (75.4% yield) of the product as a dark red syrup. $^1$H NMR showed residual triethylamine. TLC (98:2 ethanol-triethylamine) $R_f$=0.28; $^1$H NMR (CDCl$_3$) 2.53 (t, 2H, J=8.0 Hz), 2.31 (t, 2H, J=5 Hz), 2.27 (s, 4 H), 2.26 (s, 4H), 1.99 (s, 3H), 1.71 (m, 2H), 1.50 (m, 2H).

1 4-Cyclohexadiene-1-pentanoic acid, 2,5-bis(1-aziridinyl)-4-methyl-3,6-dioxo-, 2,3,5,6-tetrafluorophenyl ester (4)

To a solution of 100 mg. (0.246 mmol) of 4.6 in 7 mL of dry methylene chloride was added 144 μL (1.03 mmol) of dry triethylamine. The flask was flushed with argon and cooled in an ice bath. A solution of 92.4 μL (0.492 mmol) of 2,3,5,6-tetrafluorophenyl trifluoroacetate in 7 mL of dry methylene chloride was added to the flask over 30 minutes. TLC showed incomplete reaction. Another 90 μL TFP-TFA in 7 mL dry methylene chloride was added, over 30 minutes. The solvents were evaporated, and the product was purified by flash chromatography (5×40 cm silica) using 4:1 hexanes-ethyl acetate (2% triethylamine). The fractions containing product were evaporated to give 61 mg (42.9% yield) of the desired product 4 as a red solid: mp=110–114° C.; TLC (2:1 hexanes-ethyl acetate) $R_f$=0.56; $^1$H NMR (CDCl$_3$) 7.01 (m, 1H), 2.75 (t, 2H, J=7.2 Hz), 2.61 (t, 2H, J=8.1 Hz), 2.33 (s, 4H), 2.30 (s, 4H), 2.03 (s, 3H), 1.89 (m, 2H), 1.59 (m, 2 H). Anal. Calcd for C$_{22}$H$_{20}$F$_4$N$_2$O$_4$: C, 58.41; H, 4.46; N, 6.19. Found: C, 58.47; H, 4.86; N, 5.88.

Synthesis of Acridine Conjugate, Compound 5

1,4-Cyclohexadiene-1-pentamide, N-[6-(9-acridinylamino)hexvl]-2,5-bis(1-aziridinyl)-4-methyl-3,6-dioxo- (5)

To a solution of 76 mg (0.168 mmol) of TFP ester 4 in 3 mL of chloroform was added 94 μL of triethylamine (0.67 mmol). 1.23 ml of a 50 mg/mL solution of 9-(6-aminohexylamino)acridine dihydrochloride in methanol (61.5 mg, 0.168 mmol) was added to the stirred solution. HPLC analysis after 1 hour showed complete reaction of the starting TFP ester. The reaction mixture was partitioned between 15 mL of methylene chloride and 10 mL of water. The organic phase was washed with 10 mL of water, dried over sodium sulfate, and concentrated in vacuo. The residue was chromatographed on silica gel and the desired product was eluted with a gradient of 90:5:5-methylene chloride:triethylamine:methanol in hexanes. Removal of solvents gave the desired product 5 as a red solid: TLC (90:5:5-methylene chloride: triethylamine:methanol) $R_f$=0.79; $^1$H NMR (CDCl$_3$) δ 8.12 (d, 2H, J=8.8 Hz,), 8.07 (d, 2H, J=8.8 Hz), 7.68 (t, 2H, J=6.9 Hz), 7.37 (t, 2H, J=7.4 Hz), 5.60 (s, 1H), 5.2 (br s, 1H), 3.82 (t, 2H, J=7.1 Hz), 3.21 (q, 2H, J=6.6 Hz), 2.54 (m, 2H), 2.2 (m, 10H), 1.98 (s, 3 H), 1.8–1.65 (m, 6H), 1.5–1.3 (m, 6H).

Synthesis of CDPI$_2$ Conjugate, Compound 6

3-[1,4-Cyclohexadiene-1-pentamidyl,-2,5-bis(1-aziridinyl)-4-methyl-3,6 -dioxo-]1,2-dihydro-3H-pyrrolo[3,2-e] indole-7 carboxylate dimer methyl ester (6).

A solution of 48 mg (0.12 mmol) of freshly prepared 1,2-dihydro-3H-pyrrolo[3,2-e]indole-7 carboxylate dimer methyl ester (available in accordance with the literature procedure of Boger et al. J. Org. Chem. 1987, 52, 1521–1530) in 10 mL of dry DMF was stirred with 0.5 mL of triethylamine and 59 mg (0.13 mmol) of TFP ester 4. After 3 hours, the reaction was quenched by adding 20 mL of 10% concentrated ammonia in methanol. The mixture was cooled to −20° C. and the precipitate was recovered by centrifugation and washed twice with 30 mL of methanol to give 60 mg of crude product. 33 mg of this product was dissolved in 1 mL of DMSO and the heterogeneous mixture was centrifuged. The supernatant was poured into 5 mL of methanol, cooled to 0–5° C. The precipitate was filtered, washed with methanol and ether, and dried in vacuo to give 6.6 mg of tan solid. $^1$H NMR (d6-DMSO) δ 12.0 (s, 1H), 11.7 (s, 1H), 8.3 (br d, 1H), 8.19 (d, 1H, J=8.8 Hz), 7.33 (d, 1H, J=8.8 Hz), 7.27 (d, 1H, J=8.6 Hz), 7.13 (s, 1H), 7.01 (s, 1H), 4.61 (t, 2H, J=8.7 Hz), 4.19 (t, 2H, J=8.6 Hz), 3.88 (s, 3H), 3.5–3.2 (m, 8H), 2.24 (s, 4H), 2.21 (s, 4H), 1.88 (s, 3H), 1.61 (m, 2H), 1.46 (m, 2H).

Synthesis of ODNs and ODN-cross-linker Conjugates

Synthesis and Purification of Oligodeoxynucleotides

ODNs were prepared on an Applied Biosystems Model 394 synthesizer using the 1 μmole protocols supplied by the manufacturer. Protected β-cyanoethyl phosphoramidites, CPG supports, deblocking solutions, cap reagents, oxidizing solutions, and tetrazole solutions were purchased from Glen Research (Sterling, Va.). The sequences of the 65-mer ds DNA target of SEQUENCE ID No. 7 and of the triplex forming ODN of SEQUENCE ID No. 1, are shown above. Underlining in the sequence of the ds ODN of SEQUENCE ID No. 7 shows the position of the dG residues that are alkylated by the ODN-cross-linker conjugates of the invention.

The 3'-hexanol modification was introduced into the ODN of SEQUENCE ID No. 1 by using 2 μmol of a hexanol modified CPG support as described by Gamper et al. (1993) Nucleic Acids Res. 21 145–150, and a 5'-aminohexyl linker was introduced using N-MMT-hexanolamine phosphoramidite (Glen Research). Preparative HPLC purification, detritylation, and butanol precipitation of the synthetic ODNs was carried out as previously described by Gamper et al. supra. 0.2 mg aliquots of the 65-mer ODN of SEQUENCE ID No. 7 for triplex crosslinking experiments were further purified by preparative gel electrophoresis.

Characterization of ODNs

The concentrations of all ODNs were determined from the UV absorbance at 260 nm in phosphate buffered saline (pH 7.2). An extinction coefficient for each ODN was determined using a nearest neighbor model. For ODN-NH$_2$, E was used to calculate a theoretical ratio of concentration to A$_{260}$ of 29.1 μg/mL per OD unit. All modified ODNs were analyzed by reverse phase HPLC. The C18 HPLC system used a 250×4.6 mm C18 column equipped with a guard column (Rainin Dynamax, 10 μm particle size, 300 angstrom pore size). A gradient of 5–65% solvent B over 30 min was used (flow rate=1 mL/min) where solvent A=0.1 M triethylammonium acetate (TEAA, pH 7.5), solvent B=acetonitrile; detection was by UV absorbance at 260 nm. Unless otherwise noted, all modified ODNs were greater than 95% pure by C18 HPLC.

Synthesis of the ODN-cross-linker Conjugates, ODNs of SEQUENCE ID Nos. 2–6

The dried, de-tritylated ODN of SEQUENCE ID No. 1 was dissolved in 0.5 mL of water and injected on a Hamilton PRP-1 column (Reno, Nev.) that was equilibrated with 0.1 M TEAB (pH 7.2). The TEA salt of the ODN was eluted from the column using a gradient of 0–60% acetonitrile/30 min. The desired peak (~15 min) was collected and dried in vacuo on a centrifugal evaporator. The residue was dissolved in 0.5 mL of water and the concentration was determined. A 1 mg aliquot (174 $\mu$L, 71 nmol) was re-dried in a 1.7 mL Eppendorf tube and the residue was dissolved in 0.2 mL DMSO with 13 $\mu$L of ethyldiisopropylamine. A 20 mg/mL solution of TFP ester 3 in DMSO was prepared and 80 $\mu$L (1.6 mg, 2.8 $\mu$mol) was added to the ODN. The mixture was shaken for 3 hours at room temperature, then precipitated by adding to 10 mL of 2% $NaClO_4$/acetone in a 14 mL polypropylene tube. The mixture was centrifuged at 3000 rpm for 5 min and the pellet was sonicated with 2 mL of acetone and re-centrifuged. The pellet was dried in vacuo for 15 min and the crude product was stored at $-20°$ C. The crude reaction mixture was analyzed by C18 HPLC. Purification by C18 HPLC used the same gradient and column specified above. The peak eluting at 21 min was collected in ~1 mL of TEAA/acetonitrile and immediately precipitated by adding 100 $\mu$L of 3M sodium acetate and 4 mL of absolute ethanol. The mixture was centrifuged at 3000 rpm for 5 minutes and the pellet was sonicated with 2 mL of ethanol and re-centrifuged. The pellet was dried in vacuo for 15 min and the purified product was dissolved in 0.10 mL of water. A 5 $\mu$L aliquot was removed for C18 HPLC analysis and another 5 $\mu$L aliquot was removed for concentration determination. The bulk solution was immediately stored at $-20°$ C. for future use. HPLC analysis showed 97% purity. Concentration was 2.53 mg/mL (0.25 mg, 25% yield). The ODN of SEQUENCE ID No. 4 was also prepared in similar yield and purity using TBAB for the initial salt exchange. The ODN of SEQUENCE ID No. 2, and the ODN of SEQUENCE ID No. 3 were prepared from the TBA salts. The ODNs of SEQUENCE ID Nos. 5 and 6 were prepared from the TEA salts.

Aqueous Reactivity of ODN-cross-linker Conjugates by HPLC

HPLC Assay for Kinetics Studies

Reverse phase HPLC analysis of ODN-cross-linker conjugates used a Rainin Gradient HPLC system (Emeryville, Calif.) equipped with 10 mL pump heads and a Rainin Dynamax PDA-1 photodiode array detector. For kinetics studies, 10 $\mu$L of each sample was injected on a 4.6×150 mm Rainin Microsorb C18 column and eluted using a gradient of 5–65% acetonitrile in 0.1 M triethylammonium acetate (pH 7.5) over 20 min (flow rate=1 mL/min). ODN products were detected by UV absorbance at 260 nm and data was integrated and analyzed using Rainin Dynamax software.

Reaction of the ODNs Conjugates SEQUENCE ID Nos. 2–5 with a Model Nucleophile

100 $\mu$L of a 0.1 mM solution of the ODN of SEQUENCE ID No. 2–5, respectively, was prepared in 20 mM HEPES buffer (pH 7.2) with 140 mM KCl and 10 mM $MgCl_2$. In addition, sodium thiosulfate (10 mM, 100 equivalents) was added to the mixtures. The 0.1 mM stock solution was immediately aliquoted to 6 Eppendorf tubes that were submerged in a 37° C. bath. Aliquots were removed at various time points and immediately frozen ($-20°$ C.), and thawed just prior to HPLC analysis. Intact ODN-cross-linker conjugates eluted at ~12.5 min and a mixture of reaction products eluted at 6–12 min. A set of chromatograms were obtained in this manner. After integration, the percent intact ODN-cross-linker conjugate was plotted vs. time, and half-life for disappearance of starting conjugate was determined from the line of best fit using an equation for exponential decay. The half-life data for ODN-cross-linker conjugates of SEQUENCE ID Nos. 2–5 are given in Table 1. As noted above, the ODN of SEQUENCE ID No. 5 showed significant reaction in this assay only after reduction to the corresponding hydroquinone.

Electrophoretic Assay for DNA Crosslinking

Determination of DNA Alkylation Efficiency by the Triplex Forming ODN-cross-linker conjugates of SEQUENCE ID Nos. 2–6

The duplex of SEQUENCE ID No. 7 was used in these studies. This 65-mer contained a 33 bp homopurine-homopyrimidine run. The purine-rich strand of the duplex of SEQUENCE ID No. 7 was 5'-end labeled by treatment with T4 polynucleotide kinase and [$\gamma$-$^{32}$P]ATP under standard conditions, as described for example by Ausubel et al. in Current Protocols of Molecular Biology (1989) John Wiley, New York. The labeled ODN was purified using a Nensorb column (NEN Research Products) and had a specific activity of ~6000 cpm/fmol. Duplexes were formed by annealing 20 nM of the purine-rich strand with 40 nM of the complementary pyrimidine-rich strand in 20 mM HEPES, pH 7.2, 10 mM $MgCl_2$, 1 mM spermine, 140 mM KCl using an incubation profile of 1 min at 95° C. and 30 min at 37° C. After annealing, coralyne chloride (Sigma) was added to give a final concentration of 10 $\mu$M. The concentration of labeled duplex of of SEQUENCE ID No. 7 was 20 nM and the concentration of the respective triplex forming ODN-crosslinker conjugate of of SEQUENCE ID No. 2–6, respectively 2 $\mu$M. The incubation was done in capped and siliconized polypropylene microcentrifuge tubes (0.65 mL) at 37° C. in a final volume of 25 $\mu$L. For this 22.5 $\mu$L of the labeled duplex of SEQUENCE ID No. 7 was combined with 2.5 $\mu$L of the ODN of SEQUENCE ID No. 2–6, respectively, and the solutions were incubated at 37° C. 2.5 $\mu$L aliquots were removed at various time intervals and stored frozen in 4 $\mu$L of loading buffer (80% formamide, 0.01% xylene cyanol and bromphenol blue). The aliquots were thawed and cross-linked products were electrophoretically resolved in a denaturing 8% polyacrylamide gel. The labeled bands were visualized by autoradiography and quantified using a Bio-Rad GS-250 Phosphorimager. The percent mono-alkylated labeled strand, percent bis-alkylated labeled strand, and percent unreacted labeled strand was plotted vs. time. The approximate times and extent of maximum alkylation by the ODNs of SEQUENCE ID No. 2–6, respectively are shown in Table 2. It should be noted that prolonged incubation of the alkylated DNA targets resulted in de-purination and loss of alkylated products. A similar DNA alkylation experiment was performed at pH 6.2 for the diaziridinylquinone conjugate of SEQUENCE ID No. 5.

What is claimed is:

1. An oligonucleotide having the structure shown by formula (1) or formula (2)

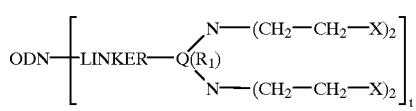   (1)

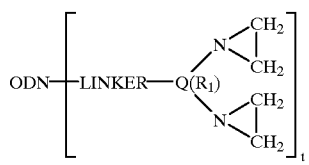   (2)

where X is a leaving group;

Q is a 5 or 6 membered aromatic or quinone ring containing 0 to 3 heteroatoms independently selected from N, O and S, the Q ring being unsubstituted or substituted with one or more $R_1$ groups where $R_1$ is F, Cl, Br, I, alkyl, Oalkyl, Salkyl, Oalkenyl, Salkenyl, CO-alkyl, OH, O=, OCOalkyl, $N(R_3)_2$, NHCOalkyl, $SO_2$alkyl, COOH, COOalkyl, CN, $CF_3$, $NO_2$, tetrazol or aryl where $R_3$ is H or alkyl, the alkyl represents normal alkyl of 1 to 10 carbons, branch-chained alkyl of 3 to 10 carbons and cycloalkyl of 3 to 10 carbons, alkenyl group represents normal alkenyl of 2 to 10 carbons, branch-chained alkenyl and cycloalkenyl of 3 to 10 carbons;

t is an integer having the values 1–3;

ODN represents an oligonucleotide sequence that is complementary to a target sequence in nucleic acid, said ODN optionally having a tail moiety attached at either of the 5' or 3' ends, or both, and optionally having a reporter group, intercalator group, minor groove binder moiety, chelating group or lipophilic group attached to it, and LINKER is a group having the length of 1 to 20 atoms, and which covalently connects the ODN to the Q ring.

2. The oligonucleotide in accordance with claim 1, having the structure of formula (1) wherein X is selected from Cl, Br and I.

3. The oligonucleotide in accordance with claim 1 wherein Q is selected from a phenyl group optionally substituted with one or more $R_1$ groups, a 1,4-quinone group optionally substituted with one or more $R_1$ groups and 1,4-dihydroxyphenyl group optionally substituted with one or more $R_1$ groups.

4. The oligonucleotide in accordance with claim 1 having approximately 6 to 500 nucleotide units.

5. The oligonucleotide in accordance with claim 4 having approximately 6 to 200 nucleotide units.

6. The oligonucleotide in accordance with claim 1 that is triplex forming and wherein the sequence ODH is complementary in the triplex forming sense to a target sequence in double stranded nucleic acid.

7. An oligonucleotide in accordance with claim 1 where t is 1.

8. An oligonucleotide having the formula

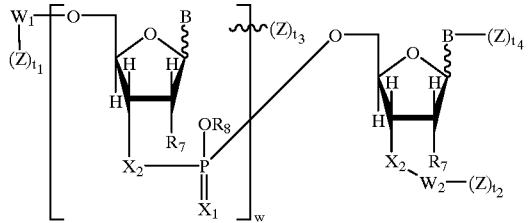

wherein

B is a heterocyclic base;

$R_1$ independently is H, O—$C_{1-6}$alkyl, $OC_{2-6}$alkenyl, or F;

$R_8$ independently is H or $C_{1-6}$alkyl;

w is an integer between approximately 5 to approximately 199;

$X_1$ is independently O or S;

$X_2$ is independently O or NH;

$t_1$ is 0 or 1;

$t_2$ is 0 or 1;

$t_3$ is an integer between 0 and 3;

$t_4$ is 0 or 1, wherein the sum of $t_1$, $t_2$, $t_3$ and $t_4$ is at least one and does not exceed 3;

$W_1$ is H, a phosphate or thiophosphate group, a tail moiety or a tail moiety attached through a phosphate moiety;

$W_2$ is H, a phosphate or thiophosphate group, a tail moiety or a tail moiety attached through a phosphate moiety, and Z represents the groups shown by formula (a) or by formula (b)

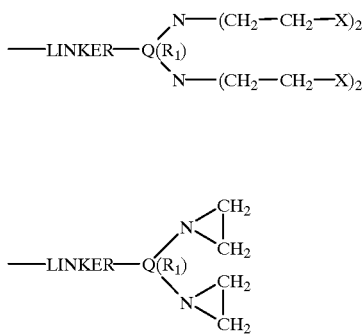

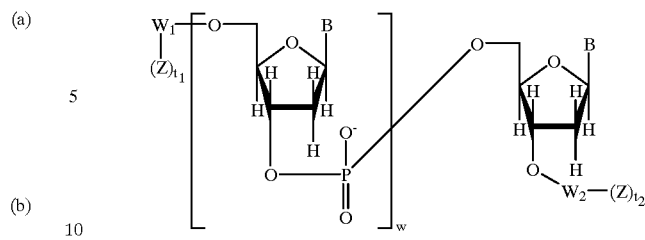

where X is a leaving group;

Q is a 5 or 6 membered aromatic or quinone ring containing 0 to 3 heteroatoms independently selected from N, O and S, the Q ring being unsubstituted or substituted with one or more $R_1$ groups where $R_1$ is F, Cl, Br, I, alkyl, Oalkyl, Salkyl, Oalkenyl, Salkenyl, CO-alkyl, OH, O=, OCOalkyl, $N(R_3)_2$, NHCOalkyl, $SO_2$alkyl, COOH, COOalkyl, CN, $CF_3$, $NO_2$, tetrazol or aryl where $R_3$ is H or alkyl, the alkyl represents normal alkyl of 1 to 10 carbons, branch-chained alkyl of 3 to 10 carbons and cycloalkyl of 3 to 10 carbons, alkenyl group normal alkenyl of 2 to 10 carbons, branch-chained alkenyl and cycloalkenyl of 3 to 10 carbons, and LINKER is a group having the length of 1 to 20 atoms, and which covalently connects the ODN to the Q ring, said oligonucleotide having a substantially continuous sequence of at least 6 nucleotides that is complementary to a target sequence in nucleic acid, and said oligonucleotide optionally having one or more covalently attached lipophilic group, a minor groove binder group, a reporter group, or chelating group.

9. The oligonucleotide in accordance with claim 8 that is triplex forming.

10. The oligonucleotide in accordance with claim 8 wherein $R_7$ is H.

11. The oligonucleotide in accordance with claim 8 wherein $X_1$ and $X_2$ are O.

12. The oligonucleotide in accordance with claim 8 wherein $t_3$ and $t_4$ each is 0.

13. The oligonucleotide in accordance with claim 8 wherein Q is selected from a phenyl group optionally substituted with one or more $R_1$ groups, a 1,4-quinone group optionally substituted with one or more $R_1$ groups and 1,4-dihydroxyphenyl group optionally substituted with one or more $R_1$ groups.

14. The oligonucleotide in accordance with claim 13 wherein Z is the group shown by formula (a) and X is Cl.

15. A triplex forming oligonucleotide that includes a substantially continuous sequence of at least 6 nucleotides, which sequence is complementary in the triplex forming sense to a target sequence in duplex nucleic acid, the oligonucleotide having the formula wherein B is a heterocyclic base;

w is an integer between approximately 5 to approximately 199;

$t_1$ is 0 or 1;

$t_2$ is 0 or 1 wherein at least one of $t_1$ and $t_2$ is 1;

$W_1$ is H, a phosphate or thiophosphate group, a tail moiety or a tail moiety attached through a phosphate moiety;

$W_2$ is H, a phosphate or thiophosphate group, a tail moiety or a tail moiety attached through a phosphate moiety, and Z represents the groups shown by formula (a) or by formula (b)

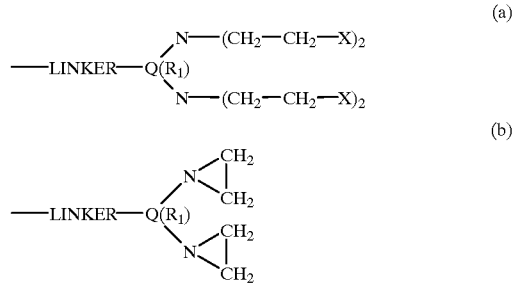

where X is a leaving group;

Q is a 5 or 6 membered aromatic or quinone ring containing 0 to 3 heteroatoms independently selected from N, O and S, the Q ring being unsubstituted or substituted with one or more $R_1$ groups where $R_1$ is F, Cl, Br, I, alkyl, Oalkyl, Salkyl, Oalkenyl, Salkenyl, CO-alkyl, OH, O=, OCOalkyl, $N(R_3)_2$, NHCOalkyl, $SO_2$alkyl, COOH, COOalkyl, CN, $CF_3$, $NO_2$, tetrazol or aryl where $R_3$ is H or alkyl, the alkyl represents normal alkyl of 1 to 10 carbons, branch-chained alkyl of 3 to 10 carbons and cycloalkyl of 3 to 10 carbons, alkenyl group normal alkenyl of 2 to 10 carbons, branch-chained alkenyl and cycloalkenyl of 3 to 10 carbons, and LINKER is a group having the length of 1 to 20 atoms, and which covalently connects the ODN to the Q ring.

16. The oligonucleotide in accordance with claim 15 wherein Z represents the group of formula (a).

17. The oligonucleotide in accordance with claim 16 wherein X is Cl.

18. The oligonucleotide in accordance with claim 15 wherein Z represents the group of formula (b).

19. The oligonucleotide in accordance with claim 17 wherein Q is selected from a phenyl group optionally substituted with one or more $R_1$ groups, a 1,4-quinone group optionally substituted with one or more $R_1$ groups and 1,4-dihydroxyphenyl group optionally substituted with one or more $R_1$ groups.

20. The oligonucleotide in accordance with claim 18 wherein Q is selected from a phenyl group optionally substituted with one or more $R_1$ groups, a 1,4-quinone group optionally substituted with one or more $R_1$ groups and 1,4-dihydroxyphenyl group optionally substituted with one or more $R_1$ groups.

21. A reagent including a cross-linking function and a functional group suitable for reacting with a nucleophilic amino group attached to an oligonucleotide while substantially retaining intact the cross-linking function, the reagent having the formula

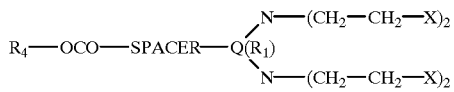

or the formula

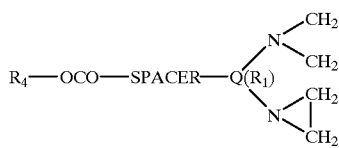

wherein X is a leaving group;
Q is a 5 or 6 membered aromatic or quinone ring containing 0 to 3 heteroatoms independently selected from N, O and S, the Q ring being unsubstituted or substituted with one or more $R_1$ groups where $R_1$ is F, Cl, Br, I, alkyl, Oalkyl, Salkyl, Oalkenyl, Salkenyl, CO-alkyl, OH, O=, OCOalkyl, $N(R_3)_2$, NHCOalkyl, $SO_2$alkyl, COOH, COOalkyl, CN, $CF_3$, $NO_2$, tetrazol or aryl where $R_3$ is H or alkyl, the alkyl represents normal alkyl of 1 to 10 carbons, branch-chained alkyl of 3 to 10 carbons and cycloalkyl of 3 to 10 carbons, alkenyl group normal alkenyl of 2 to 10 carbons, branch-chained alkenyl and cycloalkenyl of 3 to 10 carbons;
SPACER is a group having the length of 1 to 20 atoms, and which covalently connects the $R_4$ group to the Q ring, said SPACER terminating in the carbonyl (C=O) groups shown in the formula, and
$R_4$ is a leaving group, said $R_4$ leaving group forming an active ester with said carbonyl group.

22. The reagent of claim 21 wherein the $R_4$ group is 2,3,5,6-tetrafluorophenyloxy (TFP) or para-nitrophenyloxy (PNP).

23. Diaziridinyl-aryl and bis-[di(chloroethyl)amino]-aryl DNA cross-linking agents covalently bonded to DNA targeting agents, having the formula

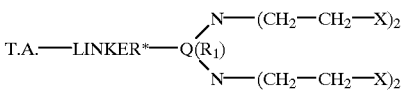

or the formula

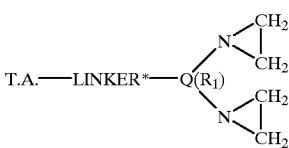

wherein X is a leaving group;
Q is a 5 or 6 membered aromatic or quinone ring containing 0 to 3 heteroatoms independently selected from N, O and S, the Q ring being unsubstituted or substituted with one or more $R_1$ groups where $R_1$ is F, Cl, Br, I, alkyl, Oalkyl, Salkyl, Oalkenyl, Salkenyl, CO-alkyl, OH, O=, OCOalkyl, $N(R_3)_2$, NHCOalkyl, $SO_2$alkyl, COOH, COOalkyl, CN, $CF_3$, $NO_2$, tetrazol or aryl where $R_3$ is H or alkyl, the alkyl represents normal alkyl of 1 to 10 carbons, branch-chained alkyl of 3 to 10 carbons and cycloalkyl of 3 to 10 carbons, alkenyl group normal alkenyl of 2 to 10 carbons, branch-chained alkenyl and cycloalkenyl of 3 to 10 carbons;
T.A. represents a DNA targeting agent selected from the group consisting of intercalators, minor groove binders, peptide nucleic acids, polyamines and synthetic polyamides.
LINKER* represents a group having the length of 1 to 60 atoms which covalently connect the DNA targeting agent to the Q ring.

24. The DNA cross-linking agents in accordance with claim 23 wherein Q is selected from a phenyl group optionally substituted with one or more $R_1$ groups, a 1,4-quinone group optionally substituted with one or more $R_1$ groups and 1,4-dihydroxyphenyl group optionally substituted with one or more $R_1$ groups.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (ODN)

<400> SEQUENCE: 1
aggagaaagg agaggagaga g                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (ODN)

<400> SEQUENCE: 2
aggagaaagg agaggagaga g                                          21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (ODN)

<400> SEQUENCE: 3
aggagaaagg agaggagaga g                                          21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (ODN)

<400> SEQUENCE: 4
aggagaaagg agaggagaga g                                          21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (ODN)

<400> SEQUENCE: 5
aggagaaagg agaggagaga g                                          21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (ODN)

<400> SEQUENCE: 6

```
aggagaaagg agaggagaga g                                             21

<210> SEQ ID NO 7
<211> LENGTH: 65
<212> TYPE: DNA
<213> ORGANISM: Homo sapiens
<220> FEATURE:
<223> OTHER INFORMATION: double stranded 65-mer that is a "homopurine
      run-containing" fragment of the human DQB1 0302
      allele

<400> SEQUENCE: 7
ctacaggctt tagcctggaa gagaaggaga gaggagagga aagaggagac aaagtgtaca    60
tttac                                                               65
```